United States Patent [19]

Mizutani et al.

[11] 3,998,868
[45] Dec. 21, 1976

[54] ALKADIENYLCYCLOPROPANECARBOXY-LATES

[75] Inventors: Toshio Mizutani, Toyonaka; Nobushige Itaya; Nobuo Ohno, both of Ikeda; Takashi Matsuo, Amagasaki; Shigeyoshi Kitamura; Yositosi Okuno, both of Toyonaka, all of Japan

[73] Assignee: Sumitomo Chemical Company, Limited, Osaka, Japan

[22] Filed: Aug. 14, 1975

[21] Appl. No.: 604,789

Related U.S. Application Data

[62] Division of Ser. No. 265,494, June 23, 1972, Pat. No. 3,954,814.

[30] Foreign Application Priority Data

June 28, 1971 Japan .............................. 46-47444

[52] U.S. Cl. ........................ 260/468 H; 260/326 R; 260/326 S; 260/326.42; 260/332.2 R; 260/346.2 R; 260/347.2; 260/347.4; 260/465 D; 260/514 H; 260/345.8; 424/274; 424/283; 424/285; 424/305; 424/275

[51] Int. Cl.² ........................................ C07C 69/74
[58] Field of Search ............................... 260/468 H

[56] References Cited
UNITED STATES PATENTS

3,723,469    3/1973    Martel ................... 260/468 H

*Primary Examiner*—Lorraine A. Weinberger
*Assistant Examiner*—Michael Shippen
*Attorney, Agent, or Firm*—Stevens, Davis, Miller & Mosher

[57] ABSTRACT

A compound of the formula,

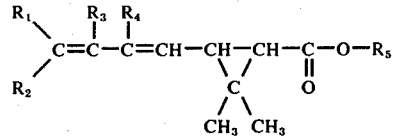

wherein $R_1$, $R_2$, $R_3$ and $R_4$ are respectively hydrogen atom or methyl, $R_5$ is a member of

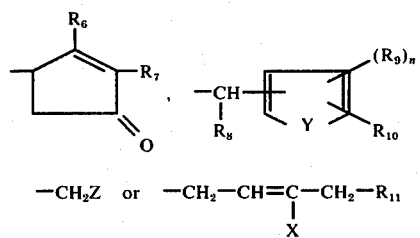

$-CH_2Z$  or  $-CH_2-CH=C-CH_2-R_{11}$
                              |
                              X wherein $R_6$ is hydrogen atom or methyl, $R_7$ is alkenyl, alkadienyl, alkynyl or benzyl, $R_8$ is hydrogen atom, ethynyl or cyano, $R_9$ is hydrogen atom, a halogen atom or alkyl, $R_{10}$ is a halogen atom, alkyl, alkenyl, alkynyl, benzyl, thenyl, furylmethyl, phenoxy, substituted phenoxy or phenylthio, or $R_9$ and $R_{10}$ are bonded at the ends to form polymethylene chain containing or not containing oxygen or sulfur atom, Y is oxygen atom, sulfur atom or $-CH=CH-$, $n$ is 1 or 2, Z is phthalimido, thiophthalimido, di- or tetra-hydrophthalimido or dialkylmaleimido, $R_{11}$ is phenyl, thienyl or furyl and X is a halogen atom, which is useful as an active ingredient of insecticides.

4 Claims, No Drawings

ALKADIENYLCYCLOPROPANECARBOXYLATES

This is a division of application Ser. No. 265,494 filed June 23, 1972 now U.S. Pat. No. 3,954,814.

This invention relates to novel cyclopropanecarboxylic acid esters, to a process for preparing the said esters, and to insecticidal compositions containing the said esters.

More particularly, the invention pertains to novel alkadienylcyclopropanecarboxylic acid esters represented by the formula (I),

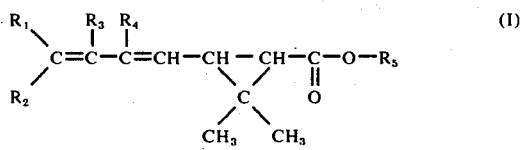

wherein $R_1$, $R_2$, $R_3$ and $R_4$ are individually hydrogen atom or methyl group; and $R_5$ is a group represented by the formula (II), (III), (IV) or (V):

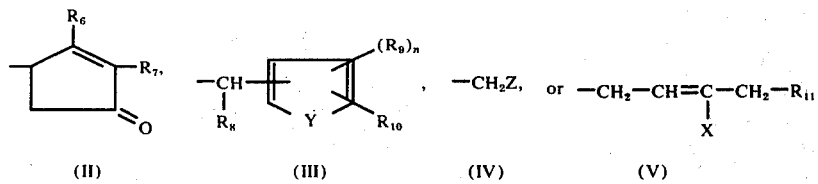

wherein $R_6$ is hydrogen atom or methyl group; $R_7$ is an alkenyl, alkadienyl, alkynyl or benzyl group; $R_8$ is hydrogen atom or ethynyl or cyano group; $R_9$ is hydrogen atom or a halogen atom or an alkyl group; $R_{10}$ is a halogen atom or an alkyl, alkenyl, alkynyl, benzyl, thenyl, furylmethyl, phenoxy, methyl-, methoxy- or chlorine-substituted phenoxy or phenylthio group, or $R_9$ and $R_{10}$ are bonded each other at the ends to form a polymethylene chain containing or not containing oxygen or sulfur atom; Y is oxygen or sulfur atom or a group of the formula —CH=CH—; n is 1 or 2; Z is a phthalimido, thiophthalimido, di- or tetrahydrophthalimido or dialkylmaleimido group; $R_{11}$ is a phenyl, thienyl or furyl group; and X is a halogen atom.

Various insecticides of the cyclopropanecarboxylic acid ester have heretofore been known, and several of such esters are present also in pyrethrum components. Among many insecticides available at present, these pyrethrum components have widely been used for the control of sanitary injurious insects and agricultural and horticultural injurious insects because of their such excellent insecticidal properties that they are not only high in insecticidal activity but also low in toxicity to mammals, quick in knock-down effect on injurious insects and scarcely make the insects resistant thereto. On the other hand, however, they are expensive and hence have such drawback as being restricted in application scope. Heretofore, many attempts have been made by a large number of researchers to synthesize various homologous compounds. These attempts, however, are directed mostly to the synthesis of alcohol components of the esters and scarcely to the synthesis of acid components.

From such a viewpoint that the above-mentioned drawbacks would be overcome by synthesizing esters having more excellent insecticidal effects, the present inventors made extensive studies particularly on acid components of the esters. As the result, the inventors have found acid components which are far more excellent in practicality than those in the conventional cyclopropanecarboxylic acid esters.

It is therefore an object of the present invention to provide insecticides comprising esters containing said acid components.

With an aim to investigate the relation between chemical structures and biological activities of cyclopropanecarboxylic acid ester type insecticides, the present inventors attempted the modification of side chains of chrysanthemic acids and examined the insecticidal effects of esters of said acids with various alcohols. As the result, the inventors have found that cyclopropanecarboxylic acid esters represented by the aforesaid formula (I) are not only far more prominent in killing effect but also more quick in knock-down effect on insects, and have confirmed that the said esters are low in toxicity to mammals and can be synthesized at low costs, and hence can be practically used not only as chemicals for controlling sanitary injurious insects but also as chemicals for controlling insects injurious to agriculture, horticulture and stored cereals. Based on the above finding, the inventors have accomplished the present invention.

The esters represented by the aforesaid formula (I) can be obtained by reacting an alcohol, or its halide or aryl sulfonate, of the formula (VI),

wherein $R_5$ is as defined previously; and A is hydroxy group, a halogen atom or an aryl sulfoxy group, with a cyclopropanecarboxylic acid, or its reactive derivative, of the formula (VII),

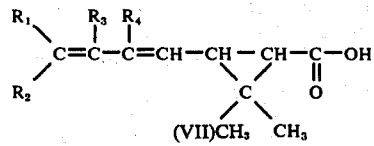

wherein $R_1$, $R_2$, $R_3$ and $R_4$ are as defined previously, if necessary in the presence of a suitable reaction auxiliary reagent.

The reactive derivative of cyclopropanecarboxylic acid which is referred to herein include acid halides, acid anhydrides, lower alkyl esters and salts.

Procedures for synthesizing the esters according to the present invention are explained in more detail below.

In case an alcohol of the formula (VI) and a carboxylic acid of the formula (VII) are used, the reaction is carried out under dehydration conditions. That is, the alcohol is reacted at room temperature or at an elevated temperature with the carboxylic acid in a suitable inert solvent in the presence of a dehydrating agent such as dicyclohexyl carbodiimide, whereby a desired ester can be obtained in a high yield.

In case an acid halide is used as a reactive derivative of the carboxylic acid of the general formula (VII), the reaction can be sufficiently accomplished at room temperature by reacting the acid halide with an alcohol of the formula (VI), using as a hydrogen halide removing reagent such an organic tertiary base as pyridine, triethylamine or the like. The acid halide used in this case may be any of the halides within the scope of the present invention, but is ordinarily an acid chloride. In the reaction, the use of a solvent is desirable for smooth progress of the reaction, and such an inert solvent as benzene, toluene or petroleum benzine is ordinarily used.

In case an acid anhydride is used as a reactive derivative of the carboxylic acid of the formula (VII), no auxiliary agent is particularly required, and the object can be accomplished by reacting the acid anhydride with an alcohol of the formula (VI). In this case, the elevation of temperature is preferable for acceleration of the reaction, and the use of an inert solvent such as toluene or xylene is preferable for smooth progress of the reaction, though not always indispensable.

In case a lower alkyl ester is used as a reactive derivative of the carboxylic acid of the formula (VII), the reaction is accomplished by reacting said ester with an alcohol of the formula (VI) at an elevated temperature in the presence of such a basic catalyst as sodium alkoxide, while removing out of the system a low boiling alcohol formed in the reaction. The use of such an inert solvent as benzene, toluene or the like is preferable for smooth progress of the reaction. The lower alkyl ester of carboxylic acid used in this case is preferably methyl ester, ethyl ester, n-propyl ester, isopropyl ester or n-butyl ester.

In case an ester of the formula (I) is desired to be obtained by use of a halide of the alcohol of the formula (VI), the carboxylic acid of the formula (VII), which is the other reactant, may be used in the form of an alkali metal salt or a salt of an organic tertiary base, or an organic tertiary base may be added, at the time of reaction, together with the carboxylic acid. In this case, it is desirable for smooth progress of the reaction that an inert solvent such as benzene or acetone is used and the system is heated to the boiling point of the solvent or to a temperature near the boiling point thereof. The halide of alcohol used in the above case is ordinarily in the form of chloride, but may be any other halide such as bromide or the like.

In the case where an ester of the formula (I) is desired to be obtained by use of an aryl sulfonate of the alcohol of the formula (VI), the other reactant and the reaction conditions are the same as in the case where the above-mentioned halide of alcohol is used. As the aryl sulfonate, a tosylate is frequently used, in general.

The cyclopropanecarboxylic acids of the formula (VII) which are used in the present invention and the esters of the formula (I) which are derived from said acids are novel compounds unknown to the literature. Among these, there are cis- and trans-isomers derived from 3-membered rings and double bonds, and optical isomers are also involved in the scope of the present invention.

The cyclopropanecarboxylic acid of the formula (VII) is a novel compound, and may be prepared easily according to the following several processes:

1. The process which comprises reacting a carbonyl compound of the formula,

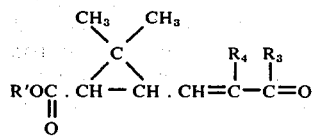

wherein $R_3$ and $R_4$ are as defined above, and $R'$ is hydrogen atom or a lower alkyl group, with a Wittig reagent of the formula,

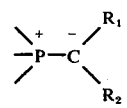

wherein $R_1$ and $R_2$ are as defined above.

2. The process which comprises reacting an aldehyde of the formula,

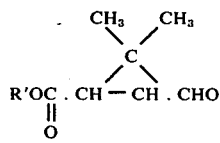

wherein $R'$ is as defined above, with a Wittig reagent of the formula,

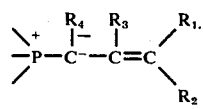

wherein $R_1$, $R_2$, $R_3$ and $R_4$ are as defined above.

3. The process which comprises reacting the carbonyl compound defined above, with an organic metal compound of the formula,

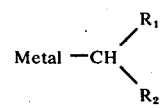

wherein $R_1$ and $R_2$ are as defined above, and Metal is lithium or a halogenomagnesium, to obtain an alcohol compound of the formula,

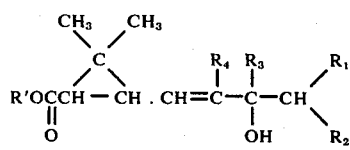

wherein $R_1$, $R_2$, $R_3$ and $R_4$ are as defined above, and dehydrating the alcohol compound.

4. The process which comprises reacting the aldehyde defined above, with an organic metal compound of the formula,

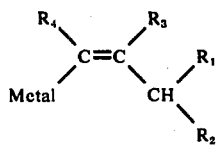

wherein $R_1$, $R_2$, $R_3$, $R_4$ and Metal are as defined above, to obtain an alcohol compound of the formula,

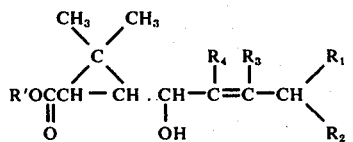

wherein $R_1$, $R_2$, $R_3$, $R_4$ and $R'$ are as defined above, dehydrating the resulting alcohol.

The reaction in the processes 1 and 2 is a so-called Wittig reaction, and the reagent used in the reaction may be prepared by the reaction between the corresponding phosphonium salt and strong basic reagents such as NaH and NaNH$_2$.

The reaction in the processes 3 and 4 is represented by the Grignard reaction. The Grignard reagent can attack the carbonyl group predominantly without the attack to the acid portion or the ester portion by using an equimolar amount of the organic metal compound, whereby the objective cyclopropanecarboxylic acid can be obtained in a high yield.

In these processes, a starting material having the group represented by $R_5$ in place of the atom or group represented bY $R'$ may be used, if it is stable in the reaction, whereby the objective ester of the formula (I) may be obtained directly.

The halides of the alcohols represented by the formula (VI) can be easily obtained by halogenating the alcohols with a thionyl halide or phosphorus halide, while the aryl sulfonates of said alcohols can be readily obtained by reacting the alcohols with an aryl sulfochloride. Further, the reactive derivatives of the carboxylic acids represented by the formula (VII), i.e. acid halides, acid anhydrides, salts and lower alkyl esters, can be easily obtained by treating the carboxylic acids according to a known process, e.g. a process adopted in the case of chrysanthemic acids.

Typical examples of alcohols of the formula (VI) and cyclopropanecarboxylic acids of the formula (VII) which are used in the present invention and those of esters of the formula (I) which are derived therefrom are as shown below, but these examples are only illustrative but not limitative.

2-Allyl-3-methyl-2-cyclopentene-1-one-4-ol
2-(2',4'-Pentadienyl)-3-methyl-2-cyclopentene-1-one-4-ol
2-Propargyl-3-methyl-2-cyclopentene-1-one-4-ol
2-Benzyl-2-cyclopentene-1-one-4-ol
5-Benzyl-3-furylmethyl alcohol
5-(2'-Thenyl)-3-furylmethyl alcohol
5-Furfuryl-3-furylmethyl alcohol
5-Benzyl-2-thenyl alcohol
3-Benzylbenzyl alcohol
5-Allylfurfuryl alcohol
5-Propargylfurfuryl alcohol
5-Propargyl-2-thenyl alcohol
4-Allylbenzyl alcohol
4-Propargylbenzyl alcohol
2-Methyl-5-propargyl-3-furylmethyl alcohol
4,5-Tetramethylenefurfuryl alcohol
4,5-Tetramethylene-2-thenyl alcohol
4,5-Trimethylene-2-thenyl alcohol
4,5-Dimethylfurfuryl alcohol
4,5-Dimethyl-2-thenyl alcohol
5-Oxa-4,5,6,7-tetrahydrobenzofurfuryl alcohol
5-Phenoxyfurfuryl alcohol
5-Phenoxy-2-thenyl alcohol
3-Phenoxybenzyl alcohol
3-Phenylthiobenzyl alcohol
5-Benzyl-3-($\alpha$-ethynyl)-furylmethyl alcohol
5-Propargyl-$\alpha$-ethynylfurfuryl alcohol
2-Methyl-5-propargyl-3-($\alpha$-ethynyl)-furylmethyl alcohol
3-Phenoxy-$\alpha$-ethynylbenzyl alcohol
5-Benzyl-3-($\alpha$-cyano)-furylmethyl alcohol
3-Phenoxy-$\alpha$-cyanobenzyl alcohol
3-(o-Tolyloxy)-$\alpha$-cyanobenzyl alcohol
3-(m-Tolyloxy)-$\alpha$-cyanobenzyl alcohol
3-(p-Tolyloxy)-$\alpha$-cyanobenzyl alcohol
3-(m-Chlorophenoxy)-$\alpha$-cyanobenzyl alcohol
3-(m-Methoxyphenoxy)-$\alpha$-cyanobenzyl alcohol
3-Benzyl-$\alpha$-cyanobenzyl alcohol
N-Hydroxymethyl-3,4,5,6-tetrahydrophthalimide N-Hydroxymethylphthalimide
N-Hydroxymethylthiophthalimide
N-Hydroxymethyl-3,6-dihydrophthalimide
N-Hydroxymethyl-dimethylmaleimide
N-Hydroxymethyl-methylethylmaleimide
3-Chloro-4-phenyl-2-butene-1-ol
3-Bromo-4-phenyl-2-butene-1-ol
3-Chloro-4-(2'-thienyl)-2-butene-1-ol
3-Chloro-4-(2'-furyl)-2-butene-1-ol
2,2-Dimethyl-3-(2'-methyl-1',3'-butadienyl)-cyclopropanecarboxylic acid
2,2-Dimethyl-3-(1',3'-butadienyl)-cyclopropanecarboxylic acid
2,2-Dimethyl-3-(2'-methyl-1',3'-pentadienyl)-cyclopropanecarboxylic acid
2,2-Dimethyl-3-(1',3'-pentadienyl)-cyclopropanecarboxylic acid
2,2-Dimethyl-3-(2',4'-dimethyl-1',3'-pentadienyl)-cyclopropanecarboxylic acid
2,2-Dimethyl-3-(4'-methyl-1',3'-pentadienyl)-cyclopropanecarboxylic acid
2,2-Dimethyl-3-(2',3'-dimethyl-1',3'-butadienyl)-cyclopropanecarboxylic acid
2,2-Dimethyl-3-(3'-methyl-1',3'-butadienyl)-cyclopropanecarboxylic acid
2,2-Dimethyl-3-(2',3'-dimethyl-1',3'-pentadienyl)-cyclopropanecarboxylic acid
2,2-Dimethyl-3-(3'-methyl-1',3'-pentadienyl)-cyclopropanecarboxylic acid
2,2-Dimethyl-3-(2',3',4'-trimethyl-1',3'-pentadienyl)-cyclopropanecarboxylic acid
2,2-Dimethyl-3-(3',4'-dimethyl-1',3'-pentadienyl)-cyclopropanecarboxylic acid

| Compound No. | Structural formula |
|---|---|
| 1 | 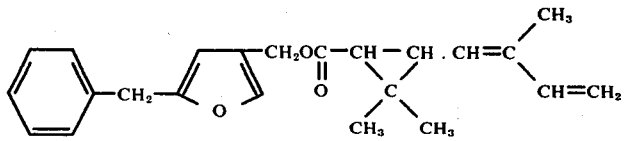<br>5-Benzyl-3-furylmethyl 2',2'-dimethyl-3'-(2''-methyl-1'',3''-butadienyl)-cyclopropanecarboxylate |
| 2 | 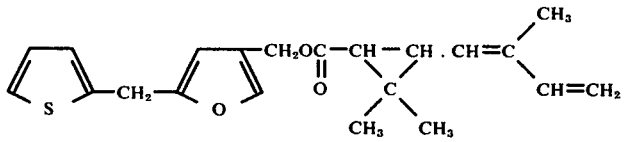<br>5-(2'-Thenyl)-3-furylmethyl 2'',2''-dimethyl-3''-(2'''-methyl-1''',3''''-butadienyl)-cyclopropanecarboxylate |
| 3 | 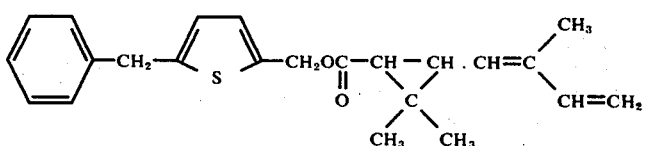<br>5-Benzyl-2-thenyl 2',2'-dimethyl-3'(2''-methyl-1'',3''-butadienyl)-cyclopropanecarboxylate |
| 4 | 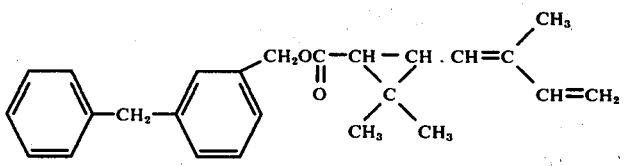<br>3-Benzylbenzyl 2',2'-dimethyl-3'-(2''-methyl-1'',3''-butadienyl)-cyclopropanecarboxylate |
| 5 | 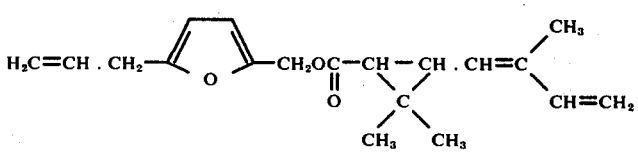<br>5-Allylfurfuryl 2',2'-dimethyl-3'-(2''-methyl-1'',3''-butadienyl)-cyclopropanecarboxylate |
| 6 | 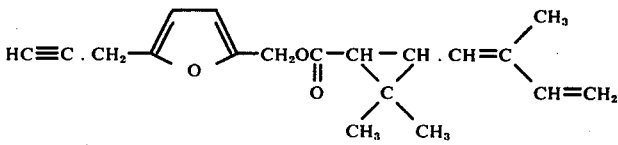<br>5-Propargylfurfuryl 2',2'-dimethyl-3'-(2''-methyl-1'',3''-butadienyl)-cyclopropanecarboxylate |
| 7 | 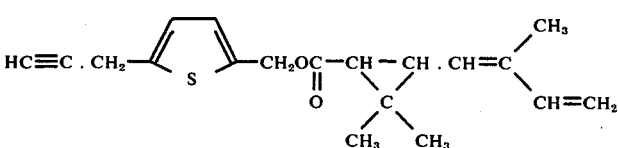<br>5-Propargyl-2-thenyl 2',2'-dimethyl-3'-(2''-methyl-1'',3''-butadienyl)-cyclopropanecarboxylate |

-continued

| Compound No. | Structural formula |
|---|---|
| 8 | 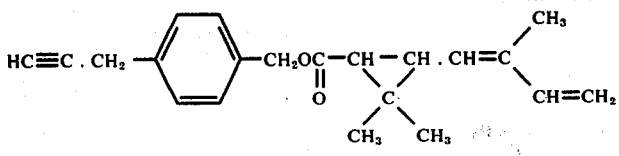 |

4-Propargylbenzyl 2',2'-dimethyl-3'-(2''-methyl-1'',3''-butadienyl)-cyclopropane-carboxylate

| 9 | 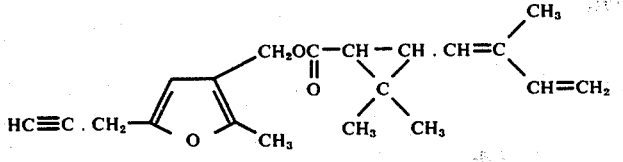 |

2-Methyl-5-propargyl-3-furylmethyl 2',2'-dimethyl-3'-(2''-methyl-1'',3''-butadienyl)-cyclopropanecarboxylate

| 10 | 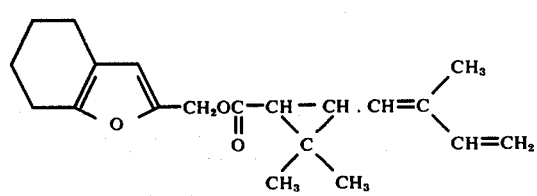 |

4,5-Tetramethylenefurfuryl 2',2'-dimethyl-3'-(2''-methyl-1'',3''-butadienyl)-cyclopropanecarboxylate

| 11 | 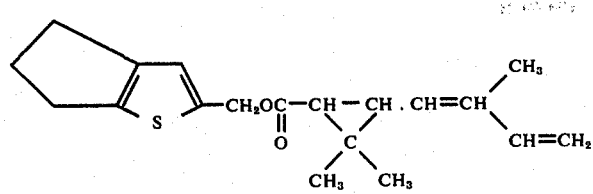 |

4,5-Trimethylene-2-thenyl 2',2'-dimethyl-3'-(2''-methyl-1'',3''-butadienyl)-cyclopropanecarboxylate

| 12 | 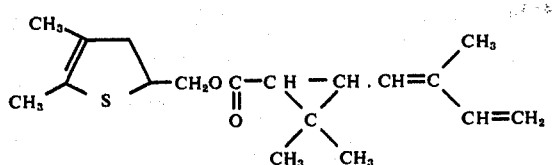 |

4,5-Dimethylfurfuryl 2',2'-dimethyl-3'-(2''-methyl-1'',3''-butadienyl)-cyclopropanecarboxylate

| 13 | 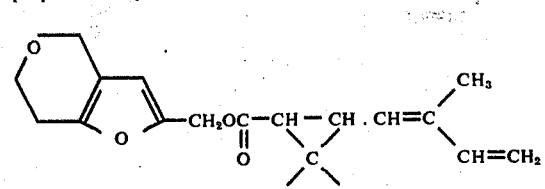 |

5-Oxa-4,5,6,7-tetrahydrobenzofurfuryl-2',2'-dimethyl-3''-(2''-methyl-1'',3''-butadienyl)-cyclopropanecarboxylate

| 14 | 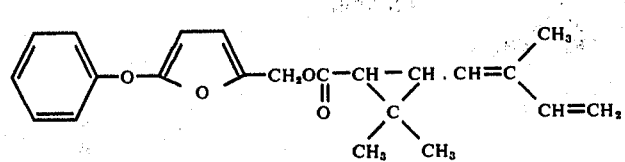 |

| Compound No. | Structural formula |
|---|---|
| | 5-Phenoxyfurfuryl 2',2'-dimethyl-3'-(2''-methyl-1'',3''-butadienyl)-cyclopropane-carboxylate |
| 15 | 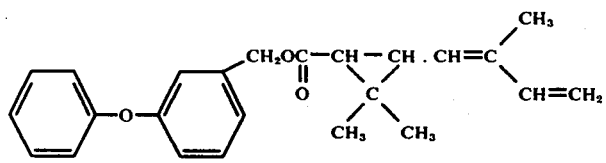 |
| | 3-Phenoxybenzyl 2',2'-dimethyl-3'-(2''-methyl-1'',3''-butadienyl)-cyclopropane-carboxylate |
| 16 | 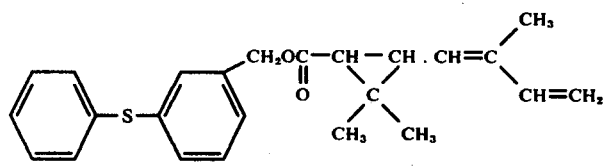 |
| | 3-Phenylthiobenzyl 2',2'-dimethyl-3'-(2''-methyl-1'',3''-butadienyl)-cyclopropanecarboxylate |
| 17 | 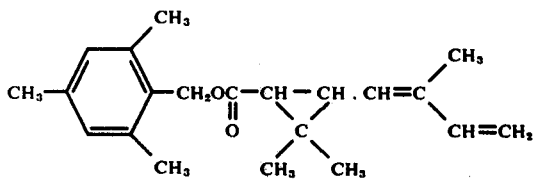 |
| | 2,4,6-Trimethylbenzyl 2',2'-dimethyl-3'-(2''-methyl-1'',3''-butadienyl)-cyclopropanecarboxylate |
| 18 | 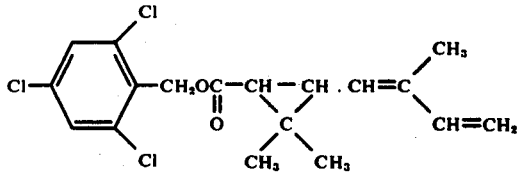 |
| | 2,4,6-Trichlorobenzyl 2',2'-dimethyl-3'-(2''-methyl-1'',3''-butadienyl)-cyclopropanecarboxylate |
| 19 | 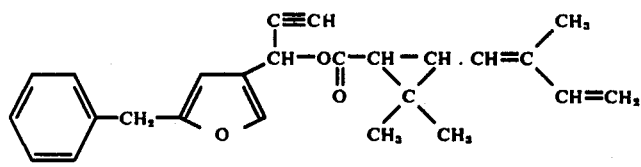 |
| | 5-Benzyl-3-(α-ethynyl)-furylmethyl 2',2'-dimethyl-3'-(2''-methyl-1'',3''-butadienyl)-cyclopropanecarboxylate |
| 20 | 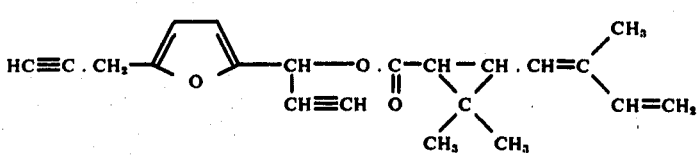 |
| | 5-Propargyl-α-ethynylfurfuryl 2',2'-dimethyl-3'-(2''-methyl-1'',3''-butadienyl)-cyclopropanecarboxylate |

-continued

| Compound No. | Structural formula |
|---|---|
| 21 | 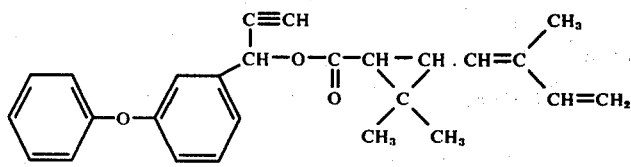<br>3-Phenoxy-α-ethynylbenzyl 2',2'-dimethyl-3'-(2''-methyl-1''',3'''-butadienyl)-cyclopropanecarboxylate |
| 22 | 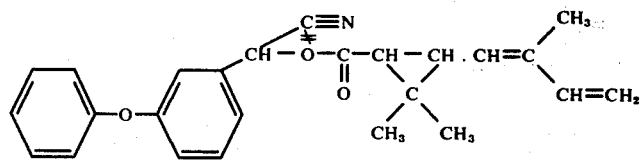<br>3-Phenoxy-α-cyanobenzyl 2',2'-dimethyl-3'-(2''-methyl-1''',3'''-butadienyl)-cyclopropanecarboxylate |
| 23 | 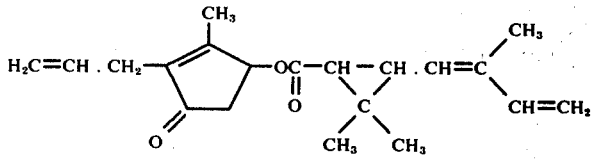<br>2-Allyl-3-methyl-2-cyclopentene-1-one-4-yl 2',2'-dimethyl-3-(2''-methyl-1''',3''-butadienyl)-cyclopropanecarboxylate |
| 24 | 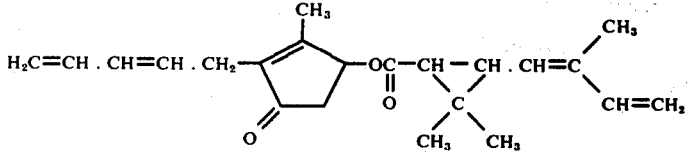<br>2-(2',4'-Pentadienyl)-3-methyl-2-cyclopentene-1-one-4-yl 2'',2''-dimethyl-3''-(2'''-methyl-1'''',3''''-butadienyl)-cyclopropanecarboxylate |
| 25 | 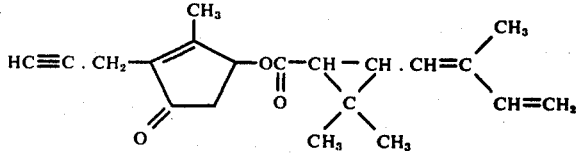<br>2-Propargyl-3-methyl-2-cyclopentene-1-one-4-yl 2',2'-dimethyl-3'-(2''-methyl-1''',3''-butadienyl)-cyclopropanecarboxylate |
| 26 | 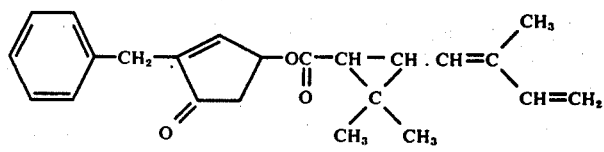<br>2-Benzyl-2-cyclopentene-1-one-4-yl 2',2'-dimethyl-3'-(2''-methyl-1''',3''-butadienyl)-cyclopropanecarboxylate |
| 27 | 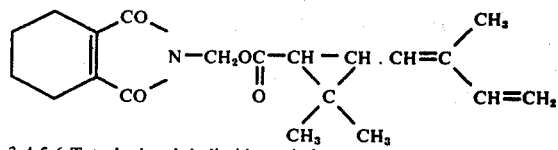<br>3,4,5,6-Tetrahydrophthalimidomethyl 2',2'-dimethyl-3'-(2''-methyl-1''',3''-butadienyl)-cyclopropanecarboxylate |

| Compound No. | Structural formula |
|---|---|
| 28 | 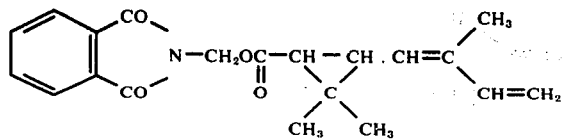<br>Phthalimidomethyl 2,2-dimethyl-3-(2'-methyl-1',3'-butadienyl)-cyclo-propanecarboxylate |
| 29 | 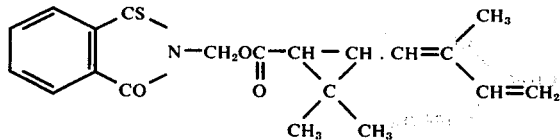<br>Monothiophthalimidomethyl 2,2-dimethyl-3-(2'-methyl-1',3'-butadienyl)-cyclo-propanecarboxylate |
| 30 | 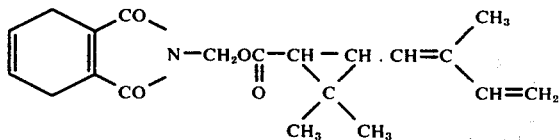<br>3,6-Dihydrophthalimidomethyl 2',2'-dimethyl-3'-(2''-methyl-1'',3''-butadienyl)-cyclopropanecarboxylate |
| 31 | 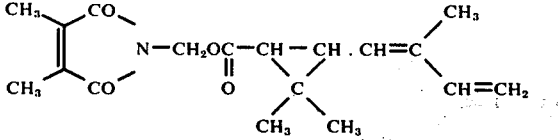<br>Dimethylmaleimidomethyl 2,2-dimethyl-3-(2'-methyl-1',3'-butadienyl)-cyclo-propanecarboxylate |
| 32 | 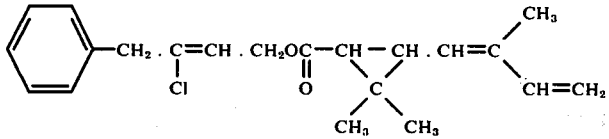<br>3-Chloro-4-phenyl-2-butene-1-yl 2',2'-dimethyl-3'-(2''-methyl-1'',3''-butadienyl)-cyclopropanecarboxylate |
| 33 | 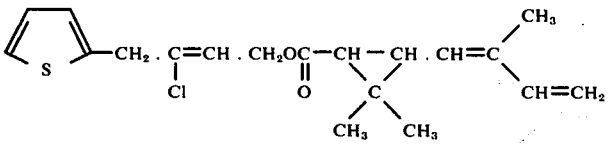<br>3-Chloro-4-(2'-thienyl)-2-butene-1-yl 2'',2''-dimethyl-3''-(2''''-methyl-1'''',3''''-butadienyl)-cyclopropanecarboxylate |
| 34 | 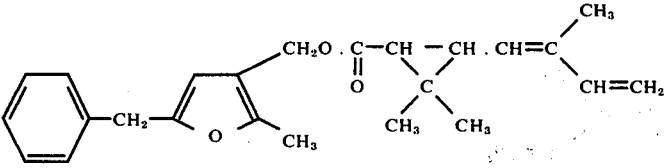<br>2-Methyl-5-benzyl-3-furylmethyl 2',2'-dimethyl-3'-(2''-methyl-1'',3''-butadienyl)-cyclopropanecarboxylate |

| Compound No. | Structural formula |
|---|---|
| 35 | 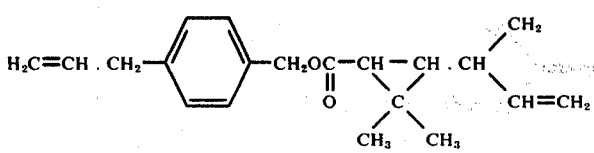<br>4-Allylbenzyl 2',2'-dimethyl-3'-(2''-methyl-1'',3''-butadienyl)-cyclopropanecarboxylate |
| 36 | 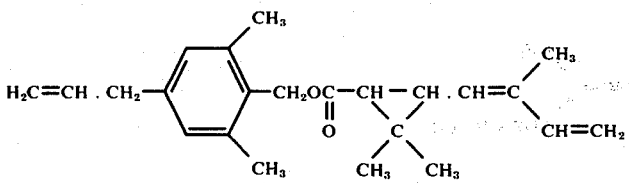<br>2,6-Dimethyl-4-allylbenzyl 2',2'-dimethyl-3'-(2''-methyl-1'',3''-butadienyl)-cyclopropanecarboxylate |
| 37 | 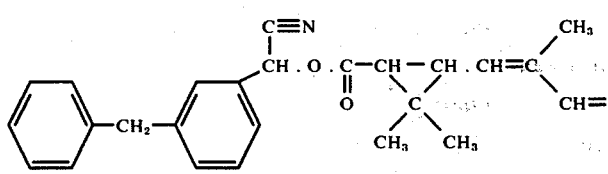<br>3-Benzyl-α-cyanobenzyl 2',2'-dimethyl-3'-(2''-methyl-1'',3''-butadienyl)-cyclopropanecarboxylate |
| 38 | 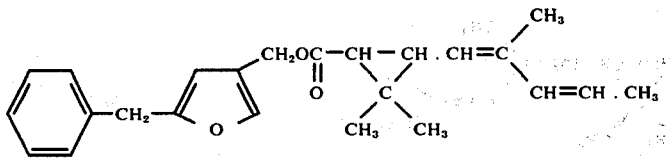<br>5-Benzyl-3-furylmethyl 2',2'-dimethyl-3'-2''-methyl-1'',3''-pentadienyl)-cyclopropanecarboxylate |
| 39 | 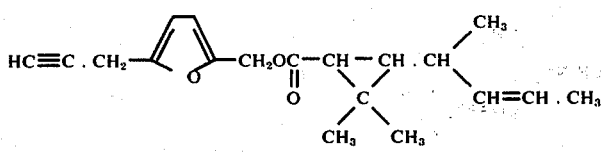<br>5-Propargylfurfuryl 2',2'-dimethyl-3'-(2''-methyl-1'',3''-pentadienyl)-cyclopropanecarboxylate |
| 40 | 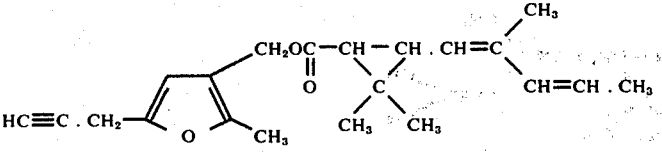<br>2-Methyl-5-propargyl-3-furylmethyl 2',2'-dimethyl-3'-(2''-methyl-1'',3''-pentadienyl)-cyclopropanecarboxylate |
| 41 | 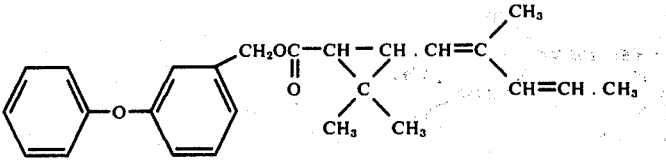<br>3-Phenoxybenzyl 2',2'-dimethyl-3'-(2''-methyl-1'',3''-pentadienyl)-cyclopropanecarboxylate |

| Compound No. | Structural formula |
|---|---|
| 42 | 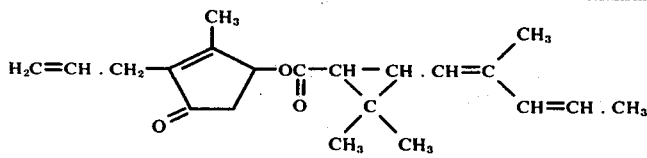
2-Allyl-3-methyl-2-cyclopentene-1-one-4-yl 2',2'-dimethyl-3'-(2''-methyl-1'',3''-pentadienyl)-cyclopropanecarboxylate |
| 43 | 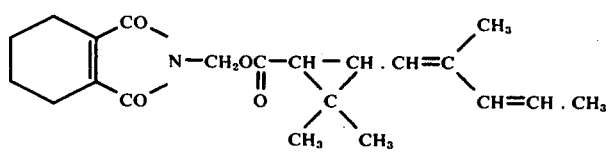
3,4,5,6-Tetrahydrophthalimidomethyl 2',2'-dimethyl-3'-(2''-methyl-1'',3''-pentadienyl)-cyclopropanecarboxylate |
| 44 | 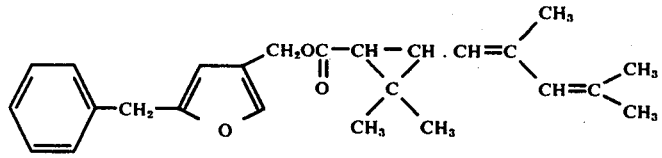
5-Benzyl-3-furylmethyl 2',2'-dimethyl-3'-(2'',4''-dimethyl-1'',3''-pentadienyl)-cyclopropanecarboxylate |
| 45 | 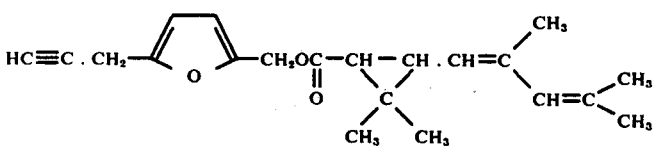
5-Propargylfurfuryl 2',2'-dimethyl-3'-(2'',4''-dimethyl-1'',3''-pentadienyl)-cyclopropanecarboxylate |
| 46 | 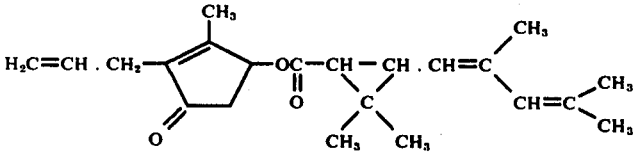
2-Allyl-3-methyl-2-cyclopentene-1-one-yl 2',2'-dimethyl-3'-(2'',4''-dimethyl-1'',3''-pentadienyl)-cyclopropanecarboxylate |
| 47 | 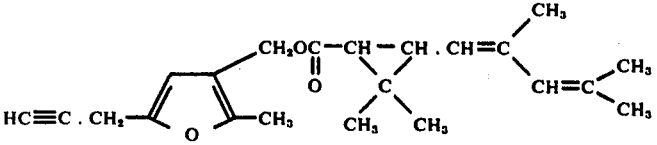
2-Methyl-5-propargyl-3-furylmethyl 2',2'-dimethyl-3'-(2'',4''-dimethyl-1'',3''-pentadienyl)-cyclopropanecarboxylate |
| 48 | 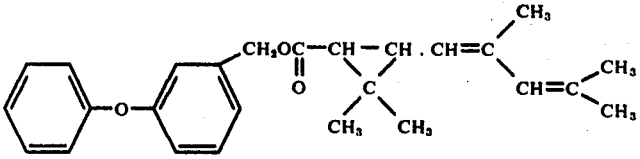
3-Phenoxybenzyl 2',2'-dimethyl-3-'-(2'',4''-dimethyl-1'',3''-pentadienyl)-cyclopropanecarboxylate |

| Compound No. | Structural formula |
|---|---|
| 49 | 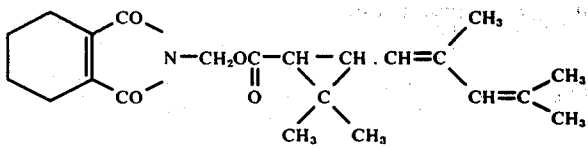<br>3,4,5,6-Tetrahydrophthalimidomethyl 2',2'-dimethyl-3'-(2'',4''-dimethyl-1'',3''-pentadienyl)-cyclopropanecarboxylate |
| 50 | 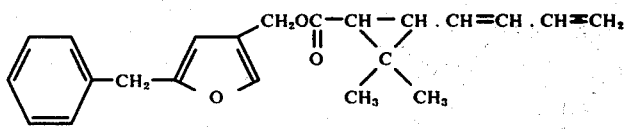<br>5-Benzyl-3-furylmethyl 2',2'-dimethyl-3'-(1'',3''-butadienyl)-cyclopropanecarboxylate |
| 51 | 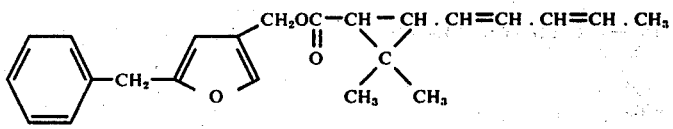<br>5-Benzyl-3-furylmethyl 2',2'-dimethyl-3'-(1'',3''-pentadienyl)-cyclopropanecarboxylate |
| 52 | 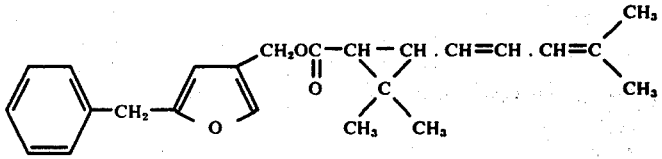<br>5-Benzyl-3-furylmethyl 2',2'-dimethyl-3'-(4''-methyl-1'',3''-pentadienyl)-cyclopropanecarboxylate |
| 53 | 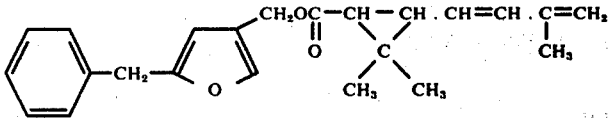<br>5-Benzyl-3-furylmethyl 2',2'-dimethyl-3'-(3''-methyl-1'',3''-butadienyl)-cyclopropanecarboxylate |
| 54 | 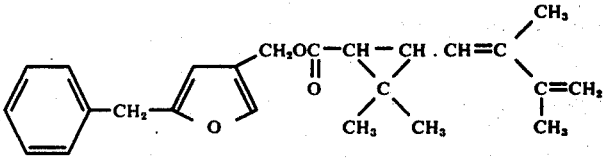<br>5-Benzyl-3-furylmethyl 2',2'-dimethyl-3'-(2'',3''-dimethyl-1'',3''-butadienyl)-cyclopropanecarboxylate |
| 55 | 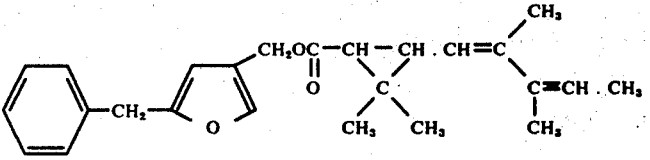<br>5-Benzyl-3-furylmethyl 2',2'-dimethyl-3'-(2'',3''-dimethyl-1'',3''-pentadienyl)-cyclopropanecarboxylate |

| Compound No. | Structural formula |
|---|---|
| 56 | 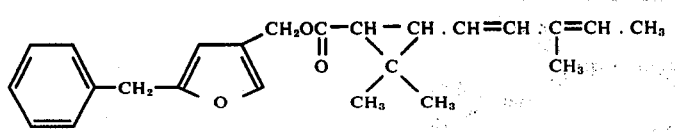 |

5-Benzyl-3-furylmethyl 2',2'-dimethyl-3'-(3''-methyl-1'',3''-pentadienyl)-cyclopropanecarboxylate

| 57 | 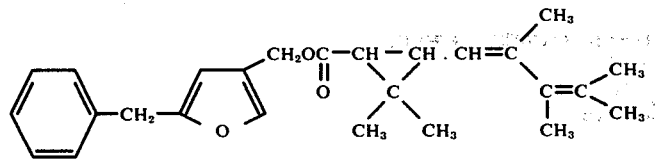 |

5-Benzyl-3-furylmethyl 2',2'-dimethyl-3'-(2'',3'',4''-trimethyl-1'',3''-pentadienyl)-cyclopropanecarboxylate

| 58 | 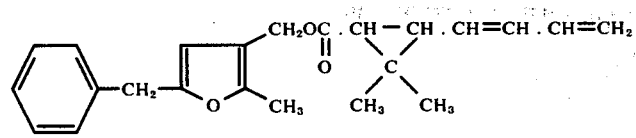 |

2-Methyl-5-benzyl-3-furylmethyl-2',2'-dimethyl-3'-(1'',3''-butadienyl)-cyclopropanecarboxylate

| 59 | 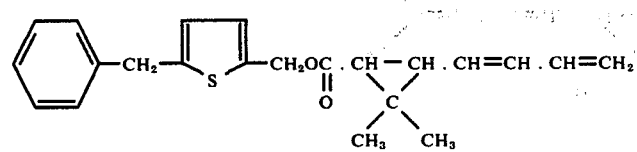 |

5-Benzyl-2-thenyl 2',2'-dimethyl-3'-(1'',3''-butadienyl)-cyclopropanecarboxylate

| 60 | 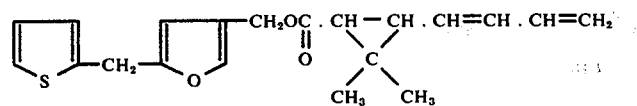 |

5-(2'-Thenyl)-3-furylmethyl 2'',2''-dimethyl-3''-(1''',3'''-butadienyl)-cyclopropanecarboxylate

| 61 | 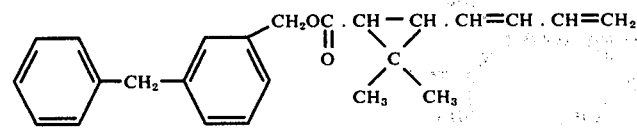 |

3-Benzylbenzyl 2',2'-dimethyl-3'-(1'',3''-butadienyl)-cyclopropanecarboxylate

| 62 | 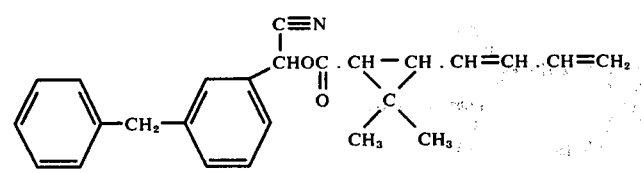 |

3-Benzyl-α-cyanobenzyl 2',2'-dimethyl-3'-(1'',3''-butadienyl)-cyclopropanecarboxylate

| Compound No. | Structural formula |
|---|---|
| 63 | 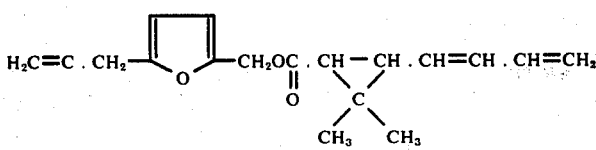 |

5-Allylfurfuryl 2',2'-dimethyl-3'-
(1'',3''-butadienyl)-cyclopropane-
carboxylate

| 64 | 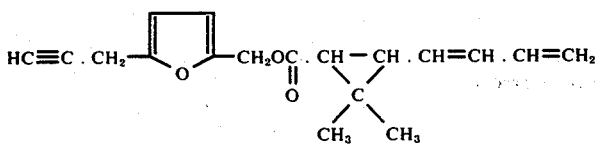 |

5-Propargylfurfuryl 2',2'-dimethyl-
3'-(1'',3''-butadienyl)-cyclopropane-
carboxylate

| 65 | 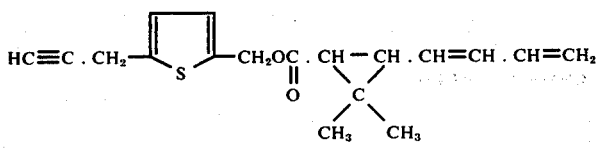 |

5-Propargyl-2-thenyl 2',2'-dimethyl-
3'-(1'',3''-butadienyl)-cyclopropane-
carboxylate

| 66 | 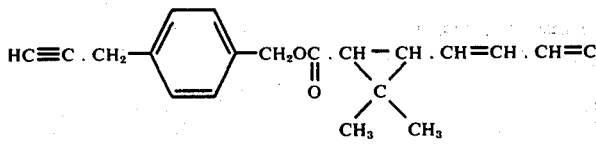 |

4-Propargylbenzyl 2',2'-dimethyl-3'-
(1'',3''-butadienyl)-cyclopropane-
carboxylate

| 67 | 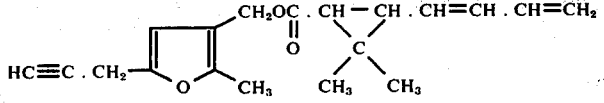 |

2-Methyl-5-propargyl-3-furylmethyl
2',2'-dimethyl-3'-(1'',3''-butadienyl)-
cyclopropanecarboxylate

| 68 | 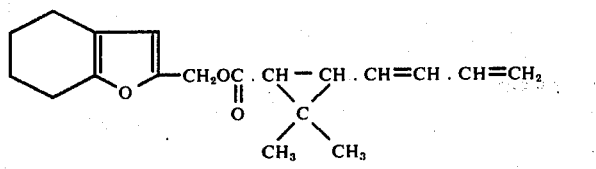 |

4,5-Tetramethylenefurfuryl 2',2'-dimethyl-
3'-(1'',3''-butadienyl)-cyclopropane-
carboxylate

| 69 | 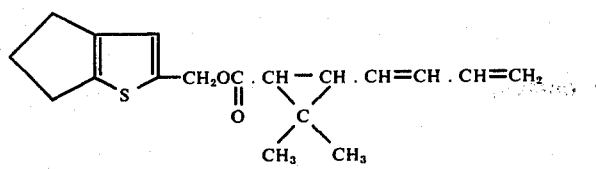 |

4,5-Trimethylene-2-thenyl 2',2'-dimethyl-
3'-(1'',3''-butadienyl)-cyclopropane-
carboxylate

| Compound No. | Structural formula |
|---|---|
| 70 | 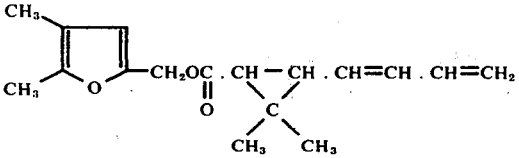 |

4,5-Dimethylfurfuryl 2',2'-dimethyl-3'-(1'',3''-butadienyl)-cyclopropane-carboxylate

| 71 | 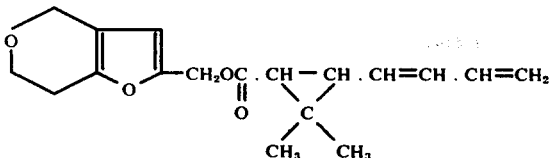 |

5-Oxa-4,5,6,7-tetrahydrobenzofurfuryl 2',2'-dimethyl-3'-(1'',3''-butadienyl)-cyclopropanecarboxylate

| 72 | 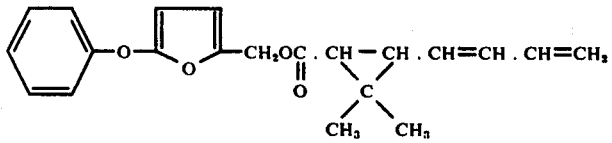 |

5-Phenoxyfurfuryl 2',2'-dimethyl-3'-(1'',3''-butadienyl)-cyclopropane-carboxylate

| 73 | 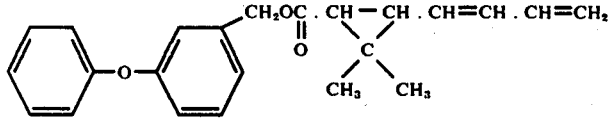 |

3-Phenoxybenzyl 2',2'-dimethyl-3'-(1'',3''-butadienyl)-cyclopropane-carboxylate

| 74 | 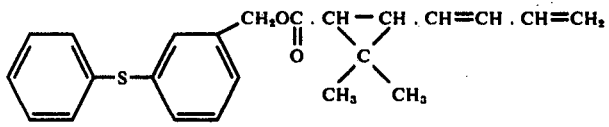 |

3-Phenylthiobenzyl 2',2'-dimethyl-3'-(1'',3''-butadienyl)-cyclopropane-carboxylate

| 75 | 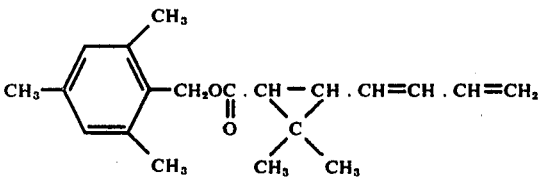 |

2,4,6-Trimethylbenzyl 2',2'-dimethyl-3'-(1'',3''-butadienyl)-cyclopropane-carboxylate

| 76 | 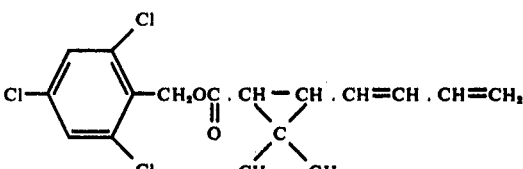 |

2,4,6-Trichlorobenzyl 2',2'-dimethyl-3'-(1'',3''-butadienyl)-cyclopropane-carboxylate

| Compound No. | Structural formula |
|---|---|
| 77 | 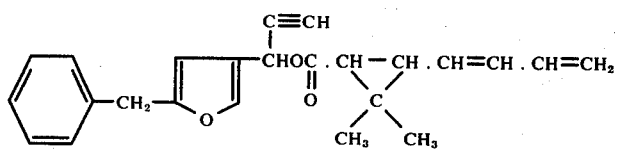<br>5-Benzyl-3-(α-ethynyl)-furylmethyl 2',2'-dimethyl-3'-(1'',3''-butadienyl)-cyclopropanecarboxylate |
| 78 | 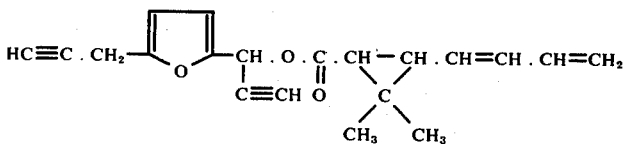<br>5-Propargyl-α-ethynylfurfuryl 2',2'-dimethyl-3'-(1'',3''-butadienyl)-cyclopropanecarboxylate |
| 79 | 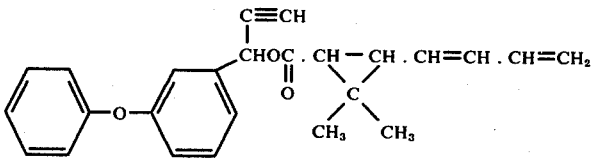<br>3-Phenoxy-α-ethynylbenzyl 2',2'-dimethyl-3'-(1'',3''-butadienyl)-cyclopropanecarboxylate |
| 80 | 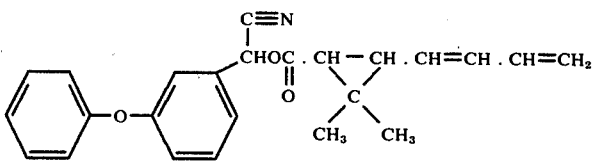<br>3-Phenoxy-α-cyanobenzyl 2',2'-dimethyl-3'-(1'',3''-butadienyl)-cyclopropanecarboxylate |
| 81 | 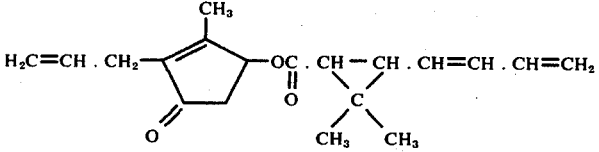<br>2-Allyl-3-methyl-2-cyclopentene-1-one-4-yl 2',2'-dimethyl-3'-(1'',3''-butadienyl)-cyclopropanecarboxylate |
| 82 | 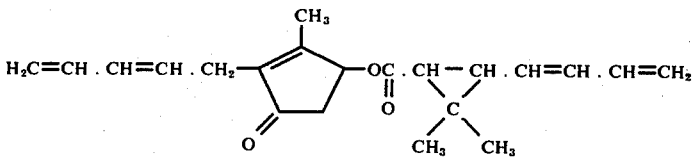<br>2-(2',4'-Pentadienyl)-3-methyl-2-cyclopentene-1-one-4-yl 2'',2''-dimethyl-3''-(1''',3'''-butadienyl)-cyclopropanecarboxylate |
| 83 | 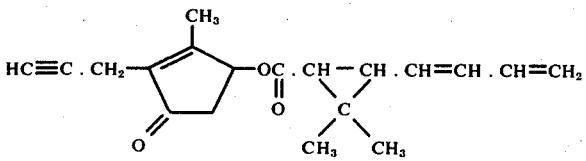<br>2-Propargyl-3-methyl-2-cyclopentene-1-one-4-yl 2',2'-dimethyl-3'-(1'',3''-butadienyl)-cyclopropanecarboxylate |

3,998,868

31                                        32

-continued

| Compound No. | Structural formula |
|---|---|

84

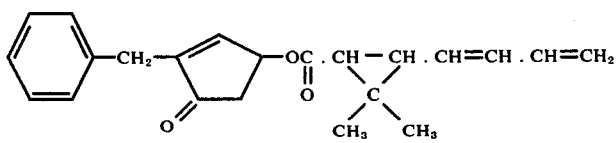

2-Benzyl-2-cyclopentene-1-one-4-yl
2',2'-dimethyl-3'-(1'',3''-butadienyl)-
cyclopropanecarboxylate

85

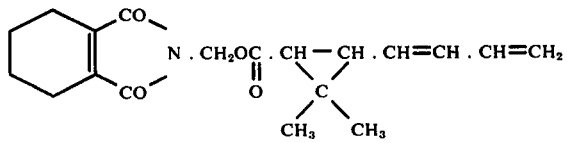

3,4,5,6-Tetrahydrophthalimidomethyl
2',2'-dimethyl-3'-(1'',3''-butadienyl)-
cyclopropanecarboxylate

86

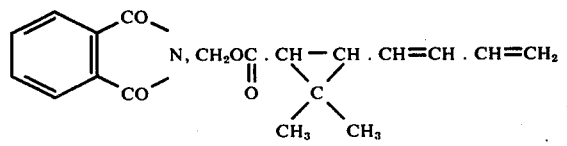

Phthalimidomethyl 2', 2'-dimethyl-3'-
(1'',3''-butadienyl)-cyclopropanecarboxylate

87

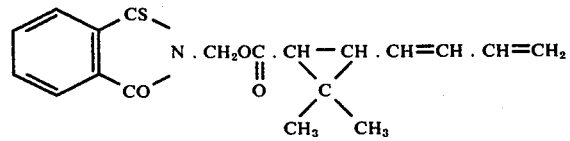

Monothiophthalimidomethyl 2',2'-dimethyl-
3'-(1'',3''-butadienyl)-cyclopropanecarboxylate

88

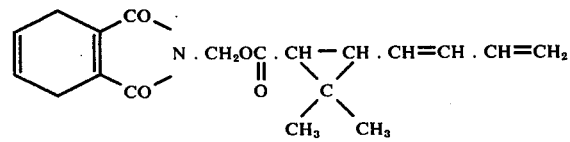

3,6-Dihydrophthalimidomethyl 2',2'-
dimethyl-3'-(1'',3''-butadienyl)-
cyclopropanecarboxylate

89

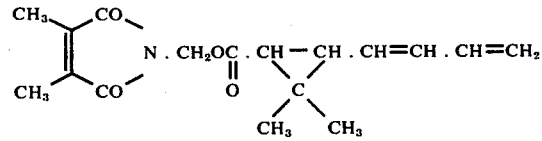

Dimethylmaleimidomethyl 2,2-dimethyl-
3-(1',3'-butadienyl)-cyclopropane-
carboxylate

90

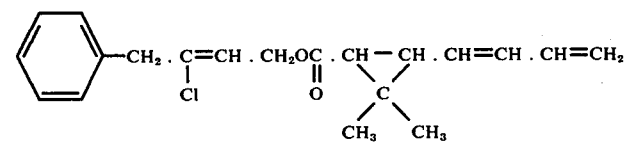

3-Chloro-4-phenyl-2-butene-1-yl 2',2'-
dimethyl-3'-(1'',3''-butadienyl)-cyclo-
propanecarboxylate

| Compound No. | Structural formula |
|---|---|
| 91 | 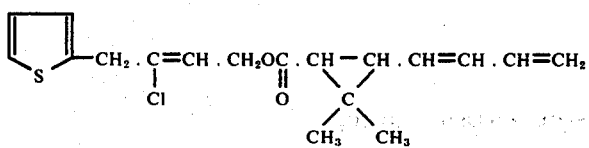<br>3-Chloro-4-(2'-thienyl)-2-butene-1-yl 2'',2''-dimethyl-3''-(1''',3'''-butadienyl)-cyclopropanecarboxylate |
| 92 | 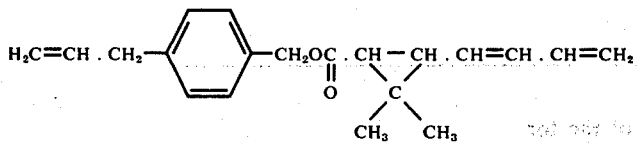<br>4-Allylbenzyl 2',2'-dimethyl-3'-(1'',3''-butadienyl)-cyclopropane-carboxylate |
| 93 | 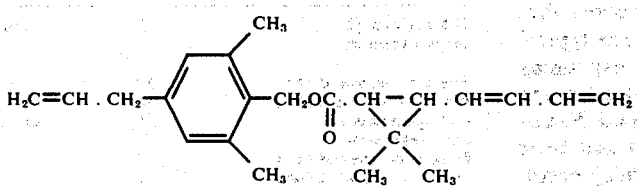<br>2,6-Dimethyl-4-allylbenzyl 2',2'-dimethyl-3'-(1'',3''-butadienyl)-cyclo-propanecarboxylate |
| 94 | 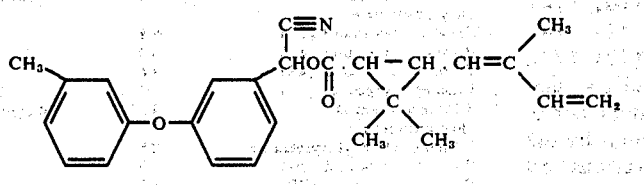<br>3-(m-Tolyloxy)-α-cyanobenzyl 2',2'-dimethyl-3'(2''-methyl-1'',3''-butadienyl)-cyclopropanecarboxylate |
| 95 | 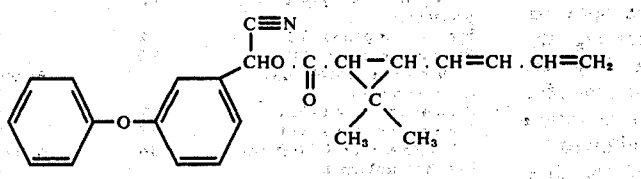<br>3-(o-Tolyloxy)-α-cyanobenzyl 2',2'-dimethyl-3'-(1'',3''-butadienyl)-cyclo-propanecarboxylate |
| 96 | 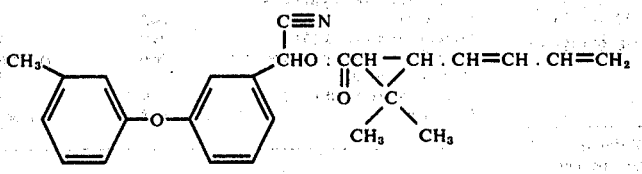<br>3-(m-Tolyloxy)-α-cyanobenzyl 2',2'-dimethyl-3'-(1'',3''-butadienyl)-cyclo-propanecarboxylate |
| 97 | 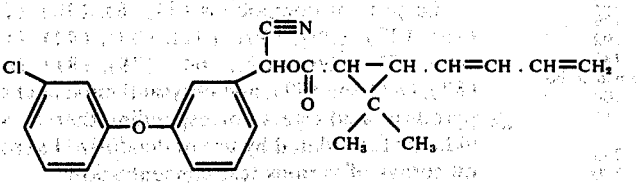<br>3-(m-Chlorophenoxy)-α-cyanobenzyl 2',2'- |

| Compound No. | Structural formula |
|---|---|
| 98 | dimethyl-3'-(1'',3''-butadienyl)-cyclopropanecarboxylate 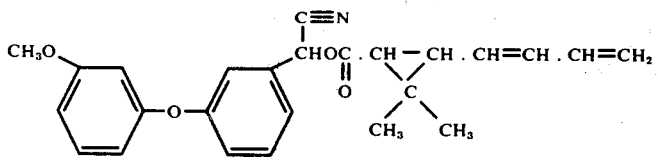 3-(m-Methoxyphenoxy)-α-cyanobenzyl 2',2'-dimethyl-3'-(1'',3''-butadienyl)-cyclopropanecarboxylate |

The cyclopropanecarboxylic acid esters of the formula (I), which are represented by the above-mentioned compounds, are more excellent in insecticidal effect and knock down effect than corresponding chrysanthemic acid esters. In order to make the above fact clearer, comparisons in effectiveness between typical compounds of the present invention and corresponding chrysanthemic acid esters and pyrethric acid esters are shown below with reference to Experimental Examples. Other compounds of the formula (I) and their geometrical isomers and optical isomers display excellent effects as well.

EXPERIMENTAL EXAMPLE 1

The present compounds (1), (4), (8), (10), (14), (15), (20), (22), (32), (36), (38), (41), (44), (48), (50), (51), (52), (53), (61), (66), (68), (72), (73), (78), (80), (81), (90), (93) and (96), and chrysanthemic acid esters and pyrethric acid esters corresponding thereto were individually formulated by use of deodorized kerosene into oil sprays of various test concentrations.

Using the Campbell's turn table [disclosed in "Soap & Sanitary Chemicals", Vol. 14, No. 6, page 119 (1938)], 5 ml. of each of the oil sprays was sprayed. When 20 seconds had elapsed after the spraying, the shutter was opened, and adults of house flies (a group of about 100 flies) were exposed to the settling mist for 10 minutes and then transferred to an observation cage. Thereafter, the flies were fed and allowed to stand at room temperature for 1 day, and then the alive and dead of the flies were observed to calculate the ratio of killed insects.

The above operation was repeated several times to measure the $LC_{50}$ (50% lethal concentration) of each compound. The results obtained were as set forth in Table 1.

Table 1

| Test compound | $LC_{50}$ (mg/100 ml) | Relative effectiveness |
|---|---|---|
| Present compound (1) | 5.3 | 188 |
| Present compound (38) | 6.6 | 152 |
| Present compound (44) | 6.3 | 159 |
| Present compound (50) | 4.4 | 227 |
| Present compound (51) | 5.6 | 179 |
| Present compound (52) | 5.2 | 192 |
| Present compound (53) | 7.1 | 141 |
| 5-Benzyl-3-furylmethyl chrysanthemate | 10 | Assumed to be 100 |
| 5-Benzyl-3-furylmethyl pyrethrate | 89 | 11 |
| Present compound (4) | 11 | 245 |
| Present compound (61) | 9 | 300 |

Table 1-continued

| Test compound | $LC_{50}$ (mg/100 ml) | Relative effectiveness |
|---|---|---|
| 3-Benzylbenzyl chrysanthemate | 27 | Assumed to be 100 |
| Present compound (8) | 50 | 170 |
| Present compound (66) | 35 | 243 |
| 4-Propargylbenzyl chrysanthemate | 85 | Assumed to be 100 |
| Present compound (10) | 12 | 133 |
| Present compound (68) | 11 | 145 |
| 4,5-Tetramethylenefurfuryl chrysanthemate | 16 | Assumed to be 100 |
| Present compound (14) | 4.7 | 181 |
| Present compound (72) | 4.1 | 207 |
| 5-Phenoxyfurfuryl chrysanthemate | 8.5 | Assumed to be 100 |
| Present compound (15) | 6.8 | 250 |
| Present compound (41) | 10 | 170 |
| Present compound (48) | 14 | 121 |
| Present compound (73) | 6 | 283 |
| 3-Phenoxybenzyl chrysanthemate | 17 | Assumed to be 100 |
| 3-Phenoxybenzyl pyrethrate | 125 | 14 |
| Present compound (20) | 9 | 289 |
| Present compound (78) | 8.2 | 317 |
| 5-Propargyl-α-ethynylfurfuryl chrysanthemate | 26 | Assumed to be 100 |
| 5-Propargyl-α-ethynylfurfuryl pyrethrate | 82 | 32 |
| Present compound (22) | 4 | 150 |
| Present compound (80) | 3.5 | 171 |
| 3-Phenoxy-α-cyanobenzyl chrysanthemate | 6 | Assumed to be 100 |
| Present compound (32) | 19 | 189 |
| Present compound (90) | 17 | 212 |
| 3-Chloro-4-phenyl-2-butene-1-yl chrysanthemate | 36 | Assumed to be 100 |
| Present compound (36) | 39 | 167 |
| Present compound (93) | 23 | 283 |
| 2,6-Dimethyl-4-allylbenzyl chrysanthemate | 65 | Assumed to be 100 |
| 2,6-Dimethyl-4-allylbenzyl pyrethrate | 142 | 46 |
| Present compound (96) | 6.0 | 150 |
| 3-(m-Tolyloxy)-2-cyanobenzyl chrysanthemate | 9.0 | Assumed to be 100 |
| Present compound (81) | 59 | 200 |
| Allethrin | 118 | Assumed to be 100 |

EXPERIMENTAL EXAMPLE 2

The present compounds (1), (6), (20), (22), (23), (25), (27), (29), (30), (31), (39), (42), (43), (45), (49), (53), (56), (62), (64), (78), (81), (83), (85), (87), (88) and (89), and chrysanthemic acid esters and pyrethric acid esters corresponding thereto were individually formulated by use of deodorized kerosene into oil sprays of various test concentrations.

About 20 adults of Northern house mosquitoes were liberated in a (70 cm)³ glass chamber, and 0.7 ml. of each of the oil sprays was sprayed into the chamber under a pressure of 1.5 kg/cm² by use of a glass atomizer. Subsequently, the number of knocked-down mosquitoes was counted to calculate the $KT_{50}$ (50 % knock down time) of each compound. The results obtained were as set forth in Table 2.

Table 2

| Test compound | Concentration of oil spray (%) | $KT_{50}$ (sec) |
|---|---|---|
| Present compound (1) | 0.2 | 131 |
| Present compound (53) | 0.2 | 124 |
| Present compound (56) | 0.2 | 150 |
| 5-Benzyl-3-furylmethyl chrysanthemate | 0.2 | 205 |
| 5-Benzyl-3-furylmethyl pyrethrate | 0.2 | 182 |
| Present compound (6) | 0.2 | 105 |
| Present compound (39) | 0.2 | 114 |
| Present compound (45) | 0.2 | 117 |
| Present compound (64) | 0.2 | 98 |
| 5-Propargylfurfuryl chrysanthemate | 0.2 | 132 |
| Present compound (20) | 0.1 | 102 |
| Present compound (78) | 0.1 | 93 |
| 5-Propargyl-α-ethynylfurfuryl chrysanthemate | 0.1 | 120 |
| Present compound (22) | 0.1 | 168 |
| Present compound (62) | 0.1 | 144 |
| 3-Phenoxy-α-cyanobenzyl chrysanthemate | 0.1 | 230 |
| Present compound (25) | 0.1 | 190 |
| Present compound (43) | 0.1 | 197 |
| Present compound (83) | 0.1 | 183 |
| 2-Propargyl-3-methyl-2-cyclopentene-1-one-4-yl chrysanthemate | 0.1 | 249 |
| Present compound (27) | 0.1 | 83 |
| Present compound (49) | 0.1 | 86 |
| Present compound (85) | 0.1 | 74 |
| 3,4,5,6-Tetrahydrophthalimidomethyl chrysanthemate | 0.1 | 103 |
| Present compound (29) | 0.2 | 182 |
| Present compound (87) | 0.2 | 177 |
| Monothiophthalimidomethyl chrysanthemate | 0.2 | 207 |
| Present compound (30) | 0.1 | 89 |
| Present compound (88) | 0.1 | 79 |
| 3,6-Dihydrophthalimidomethyl chrysanthemate | 0.1 | 107 |
| Present compound (31) | 0.1 | 80 |
| Present compound (89) | 0.1 | 72 |
| Dimethylmaleimidomethyl chrysanthemate | 0.1 | 101 |
| Present compound (23) | 0.2 | 152 |
| Present compound (42) | 0.2 | 165 |
| Present compound (81) | 0.2 | 141 |
| Allethrin | 0.1 | 292 |
| Allethrin | 0.2 | 197 |
| 2-Allyl-3-methyl-2-cyclopentene-1-one-4-yl pyrethrate | 0.2 | 173 |

EXPERIMENTAL EXAMPLE 3

The present compounds (1), (4), (8), (10), (14), (15), (22), (32), (36), (38), (41), (44), (48), (50), (51), (52), (53), (61), (66), (68), (72), (73), (80), (81), (90) and (93) are chrysanthemic acid esters corresponding thereto were individually dissolved in acetone to prepare insecticides of various concentrations. Using a micro dropping means, each of the insecticides was dropped to the head and tail of hibernating rice stem borer larvae. 3 Days thereafter, the alive and dead of the larvae were observed to calculate the $LD_{50}$ (50 % lethal dose) of each compound. The results obtained were as set forth in Table 3.

Table 3

| Test Compound | $LD_{50}$ (γ/larva) | Relative effectiveness |
|---|---|---|
| Present compound (1) | 0.068 | 294 |
| Present compound (38) | 0.102 | 196 |
| Present compound (44) | 0.145 | 138 |
| Present compound (50) | 0.057 | 351 |
| Present compound (51) | 0.065 | 308 |
| Present compound (52) | 0.100 | 200 |
| Present compound (53) | 0.170 | 118 |
| 5-Benzyl-3-furylmethyl chrysanthemate | 0.20 | Assumed to be 100 |
| Present compound (4) | 0.71 | 169 |
| Present compound (61) | 0.50 | 240 |
| 3-Benzylbenzyl chrysanthemate | 1.20 | Assumed to be 100 |
| Present compound (8) | 0.37 | 268 |
| Present compound (66) | 0.31 | 319 |
| 4-Propargylbenzyl chrysanthemate | 0.99 | Assumed to be 100 |
| Present compound (10) | 0.32 | 234 |
| Present compound (68) | 0.26 | 288 |
| 4,5-Tetramethylenefurfuryl chrysanthemate | 0.75 | Assumed to be 100 |
| Present compound (14) | 0.040 | 300 |
| Present compound (72) | 0.034 | 353 |
| 5-Phenoxyfurfuryl chrysanthemate | 0.12 | Assumed to be 100 |
| Present compound (15) | 0.29 | 248 |
| Present compound (41) | 0.48 | 150 |
| Present compound (48) | 0.56 | 129 |
| Present compound (73) | 0.26 | 277 |
| 3-Phenoxybenzyl chrysanthemate | 0.72 | Assumed to be 100 |
| Present compound (22) | 0.006 | 167 |
| Present compound (80) | 0.005 | 200 |
| 3-Phenoxy-α-cyanobenzyl chrysanthemate | 0.01 | Assumed to be 100 |
| Present compound (32) | 0.52 | 131 |
| Present compound (90) | 0.43 | 158 |
| 3-Chloro-4-phenyl-2-butene-1-yl chrysanthemate | 0.68 | Assumed to be 100 |
| Present compound (36) | 0.28 | 125 |
| Present compound (93) | 0.21 | 167 |
| 2,6-Dimethyl-4-allylbenzyl chrysanthemate | 0.35 | Assumed to be 100 |
| Present compound (81) | 1.7 | 153 |
| Allethrin | 2.6 | Assumed to be 100 |

As is clear from the above-mentioned Experimental Examples, the present compounds have marked killing effects on house flies and mosquitoes. Further, they show excellent killing effects on sanitary injurious insects such as cockroaches and the like and on insects injurious to stored cereals, and, nevertheless, are low in toxicity to mammals.

Owing to such characteristics, the esters of the present invention find broad uses for the prevention of epidemics and for the control of insects injurious to stored cereals. Furthermore, they are extremely useful for the control of agricultural and forestry injurious insects such as green rice leaf-hoppers, smaller brown planthoppers, rice stem borers, larvae of Japanese giant silk moth, common cabbageworms, cabbage army worms, diamond back moth, cut worms, tent catapillar, etc. Particularly, they are low toxic and harmless to mammals, and hence are freely applicable to crops before harvest, foods and packaging materials, and are usable for control of insects injurious to stored cereals and for home horticulture and green house cultivation.

In preparing the insecticidal compositions of the present invention, the present compounds may be formulated into oil sprays, emulsifiable concentrates, dusts, aerosols, wettable powders, granules, mosquito coils and other heating or non-heating fumigants according to the procedures thoroughly known to those skilled in the art, using diluting adjuvants for general insecticides like in the case of the conventional pyrethroides. Alternatively, they may be formulated into death-inducing powder or solid preparations incorporated with baits or other substances attractive for injurious insects.

Further, the present compounds can display more excellent insecticidal activities when used in combination of 2 or more, and can be enhanced in insecticidal effect when used in admixture with such synergists for pyrethroides as α-[2-(2-butoxyethoxy)-ethoxy]-4,5-methylenedioxy-2-propyltoluene (hereinafter referred to as "Piperonyl butoxide"), 1,2-methylenedioxy-4-[2-(octylsulfinyl)propyl] benzene (hereinafter referred to as "Sulfoxide"), 4-(3,4-methylenedioxyphenyl)-5-methyl-1,3-dioxane (hereinafter referred to as "Sufroxane"), N-(2-ethylhexyl)-bicyclo[2,2,1]hepta-5-ene-2,3-dicarboximide (hereinafter referred to as "MGK-264"), octachlorodipropyl ether (hereinafter referred to as "S-421") and isobornyl thiocyanoacetate (hereinafter referred to as "Thanite"), or with other known synergists effective for allethrin and pyrethrin.

When phenol derivatives such as BHT, bisphenol derivatives, or arylamines such as phenyl-α-naphthylamine, phenyl-β-naphthylamine and phenetidine-acetone condensates are added in suitable amounts as stabilizers, it is possible to obtain insecticidal compositions which have been more stabilized in effectiveness.

Furthermore, the present compounds may be used in admixture with other physiologically active materials, e.g. pyrethrin (pyrethrum extract), other known cyclopropanecarboxylic acid ester type insecticides such as allethrin, N-(chrysanthemoxymethyl)-3,4,5,6-tetrahydrophthalimide (hereinafter referred to as "Tetramethrin"), 5-benzyl-3-furylmethyl chrysanthemate (hereinafter referred to as "resmethrin"), 3-phenoxybenzyl chrysanthemate and geometrical or optical isomers thereof, organo-chlorine type insecticides such as DDT, BHC and methoxychlor, organo-phosphorus type insecticides such as 0,0-dimethyl-0-(3-methyl-4-nitrophenyl)-phosphorothioate (hereinafter referred to as "fenitrothion"), 0,0-dimethyl-0-(2,2-dichlorovinyl)-phosphate (hereinafter referred to as DDVP), 0,0-dimethyl 0-3-methyl-4-methylmercapt-phenyl phosphorothioate (trade mark: Baycid), 0,0-diethyl 0-1-(2′,4′-dichlorophenyl)-2-chloro-vinyl phosphate (trade mark: Vinyphate), dimethyldicarbethoxyethyl dithiophosphate (trade mark: Malathion), 2-methoxy-4H-1,3,2-benzodioxaphosphorin-2-sulfide (trade mark: Salithion), ethyldimethyldithiophosphorylphenyl acetate (trade mark: Papthion), dimethyl-p-cyanophenyl thiophosphate (trade mark: Cyanox), 0,0-dimethyl 1-hydroxy-2,2,2-trichloroethyl phosphonate (trade mark: Dipterex), and 2-isopropyl-4-methylpyrimidyl-6-diethyl-thiophosphate (trade mark: Diazinon), carbamate type insecticides such as 1-naphthyl-N-methylcarbamate, 3,4-dimethylphenyl-N-methylcarbamate, 3,5-dimethylphenyl-N-methylcarbamate, 2-isopropoxyphenyl-N-methylcarbamate (trade mark: Suncide), and S-methyl-N-[(methylcarbamoyl)oxy]thioacetimidate (trade mark: Lannate), such insecticides as N′-(2-methyl-4-chlorophenyl)-N,N-dimethyl formamidine (trade mark: Galecron) and 1,3-bis(carbamoylthio)-2-(N,N-dimethylamino)propane hydrochloride (trade mark: Cartap) or with other agricultural chemicals such as fungicides, nematocides, acaricides, herbicides, fertilizers, etc., whereby multi-purpose compositions excellent in effectiveness can be prepared, and synergistic effects due to blending therewith may be expected.

The process of the present invention is illustrated below with reference to examples.

In the first place, standard operational procedures for synthesis of the present compounds are explained.

A. Procedure according to the reaction of the alcohol with a halide of the carboxylic acid:

To a solution of 0.05 mole of the alcohol in 3 times the volume thereof of dry benzene is added 0.075 mole of pyridine. To this solution is added a solution of 0.053 mole of carboxylic acid chloride in 3 times the volume of said chloride of dry benzene. After allowing the reaction mixture to stand overnight in a closed vessel, a small amount of water is added to the mixture to dissolve deposited pyridine hydrochloride, and then the water layer is separated. The organic layer is washed successively with a 5% aqueous hydrochloric acid solution, a saturated aqueous sodium bicarbonate solution and a saturated aqueous sodium chloride solution, and then dried over anhydrous sodium sulfate. Thereafter, the benzene is removed by distillation, and the residue is purified according to reduced pressure distillation or column chromatography using silica gel, alumina or the like, to obtain a desired ester.

B. Procedure according to the dehydration reaction of the alcohol with the carboxylic acid:

A solution of 0.05 mole of the alcohol in 3 times the volume of said alcohol of dry benzene is mixed with a solution of 0.05 mole of the carboxylic acid in 3 times the volume of said acid of benzene. The mixed solution is incorporated with 0.08 mole of dicyclohexyl carbodiimide, and then allowed to stand overnight in a closed vessel. On the next day, the reaction mixture is heated under reflux for 2 hours to complete the reaction, and deposited dicyclohexylurea is separated by filtration. Thereafter, the same manner as in the standard operational procedure A is effected to obtain a desired ester.

C. Procedure according to the reaction of the alcohol with an anhydride of the carboxylic acid:

To a solution of 0.05 mole of the alcohol in 3 times the volume of said alcohol of toluene is added 0.05 mole of a carboxylic anhydride (synthesized from carboxylic acid and acetic anhydride), and the mixture is reacted at 100° C. for 3 hours. Subsequently, byproduced carboxylic acid is recovered by distillation or by neutralization with a 5% aqueous sodium hydroxide. Thereafter, the same manner as in the standard operational procedure A is effected to obtain a desired ester.

D. Procedure according to the reaction of a halide of the alcohol with the carboxylic acid:

A mixture comprising 0.05 mole of a halide of the alcohol and 0.06 mole of the carboxylic acid is dissolved in 3 times the volume of said mixture of acetone. Into this solution is dropped, while stirring and maintaining the solution at 15° to 20° C., a solution of 0.08 mole of triethylamine in 3 times the volume thereof of acetone. After completion of the dropping, the mixture is refluxed for 2 hours to terminate the reaction. After cooling the reaction mixture, deposited triethylamine hydrochloride is separated by filtration, and the acetone is distilled off from the filtrate. To the residue is added 3 times the volume thereof of benzene, and then the same manner as in the standard operational procedure A is effected to obtain a desired ester.

E. Procedure according to the ester exchange reaction of the alcohol with a lower alkyl ester of the carboxylic acid:

A mixture comprising 0.05 mole of the alcohol and 0.06 mole of ethyl ester of the carboxylic acid is dissolved in 5 times the volume of said mixture of dry toluene. The resulting solution is incorporated with 0.005 mole of sodium ethoxide, and then heated under reflux. Subsequently, ethanol formed with progress of the reaction is removed as an azeotropic fraction with the solvent by use of a rectifier, and the reaction mixture is charged with cold water. Thereafter, the same manner as in the standard operational procedure A is effected to obtain a desired ester.

F. Procedure according to the reaction of an aryl surfonate of the alcohol with a salt of the carboxylic acid:

To a solution of 0.05 mole of a tosylate of the alcohol in 3 times the volume thereof of acetone is gradually added with thorough stirring at room temperature 0.06 mole of a sodium salt of the the carboxylic acid (synthesized by reacting the carboxylic acid with an equimolar amount of sodium hydroxide in water and then removing the water by distillation). Thereafter, the resulting mixture is refluxed for 30 minutes to complete the reaction. After cooling the reaction mixture, a deposited solid substance is separated by filtration, and the acetone is removed by distillation from the filtrate. The residue is dissolved in 3 times the volume thereof of benzene, and then the same manner as in the standard operational procedure A is effected to obtain a desired ester.

EXAMPLES 1 – 29

The results obtained by practicing the present process according to the above-mentioned standard operational procedures were as set forth in the following table.

| Example No. | Alcohol or its derivative | Cyclopropane-carboxylic acid or its derivative | Reaction procedure | Name of compound |
|---|---|---|---|---|
| 1 | 5-Benzyl-3-furylmethyl alcohol | 2,2-Dimethyl-3-(2'-methyl-1',3'-butadienyl)-cyclopropanecarboxylic acid | B | 5-Benzyl-3-furylmethyl 2',2'-dimethyl-3'-(2''-methyl-1'',3''-butadienyl)-cyclopropanecarboxylate |
| 2 | 5-(2'-Thenyl)-3-furylmethyl alcohol | 2,2-Dimethyl-3-(2'-methyl-1',3'-butadienyl)-cyclopropanecarboxylic acid chloride | A | 5-(2'-Thenyl)-3-furylmethyl 2'',2''-dimethyl-3'-(2'''-methyl-1''',3'''-butadienyl)-cyclopropanecarboxylate |
| 3 | 5-Benzyl-2-thenyl chloride | 2,2-Dimethyl-3-(2'-methyl-1',3'-butadienyl-cyclopropane-carboxylic acid | D | 5-Benzyl-2-thenyl 2',2'-dimethyl-3'-(2''-methyl-1'',3''-butadienyl)-cyclopropanecarboxylate |
| 4 | 5-Propargylfurfuryl alcohol | 2,2-Dimethyl-3-(2'-methyl-1',3'-butadienyl)-cyclopropanecarboxylic acid chloride | A | 5-Propargylfurfuryl 2',2'-dimethyl-3'-(2''-methyl-1'',3''-butadienyl)-cyclopropanecarboxylate |
| 5 | 5-Propargyl-2-thenyl alcohol | 2,2-Dimethyl-3-(2'-methyl-1',3'-butadienyl)-cyclopropanecarboxylic acid chloride | A | 5-Propargyl-2-thenyl-2',2'-dimethyl-3'-(2''-methyl-1'',3''-butadienyl)-cyclopropanecarboxylate |
| 6 | 2-Methyl-5-propargyl-3-furylmethyl alcohol | 2,2-Dimethyl-3-(2'-methyl-1',3'-butadienyl)-cyclopropanecarboxylic acid chloride | A | 2-Methyl-5-propargyl-3-furylmethyl 2',2'-dimethyl-3'-(2''-methyl-1'',3''-butadienyl)-cyclopropanecarboxylate |
| 7 | 4,5-Tetramethylene-furfuryl alcohol | 2,2-Dimethyl-3-(2'-methyl-1',3'-butadienyl)-cyclopropanecarboxylic acid chloride | A | 4,5-Tetramethylenefurfuryl 2',2'-dimethyl-3'-(2''-methyl-1'',3''-butadienyl)-cyclopropanecarboxylate |
| 8 | 4,5-Trimethylene-2-thenyl alcohol | 2,2-Dimethyl-3-(2'-methyl-1',3'-butadienyl)-cyclopropanecarboxylic acid chloride | B | 4,5-Trimethylene-2-thenyl 2',2'-dimethyl-3'-(2''-methyl-1'',3''-butadienyl)-cyclopropanecarboxylate |
| 9 | 3-Phenoxybenzyl alcohol | 2,2-Dimethyl-3-(2'-methyl-1',3'-butadienyl)-cyclopropanecarboxylic acid anhydride | C | 3-Phenoxybenzyl 2',2'-dimethyl-3'-(2''-methyl-1'',3''-butadienyl)-cyclopropanecarboxylate |
| 10 | 5-Propargyl-α-ethynyl-furfuryl alcohol | 2,2-Dimethyl-3-(2'-methyl-1',3'-butadienyl)-cyclopropanecarboxylic acid chloride | A | 5-Propargyl-α-ethynylfurfuryl 2',2'-dimethyl-3'-(2''-methyl-1'',3''-butadienyl)-cyclopropanecarboxylate |
| 11 | 3-Phenoxy-α-cyanobenzyl alcohol | 2,2-Dimethyl-3-(2'-methyl-1',3'-butadienyl)-cyclopropanecarboxylic acid chloride | A | 3-Phenoxy-α-cyanobenzyl 2',2'-dimethyl-3'-(2''-methyl-1'',3''-butadienyl)-cyclopropanecarboxylate |
| 12 | 2-Allyl-3-methyl-2-cyclopentene-1-one-4-ol | 2,2-Dimethyl-3-(2'-methyl-1',3'-butadienyl)-cyclopropanecarboxylic acid chloride | A | 2-Allyl-3-methyl-2-cyclopentene 1-one-4-yl 2',2'-dimethyl-3' (2''-methyl-1''',3''-butadienyl)-cyclopropanecarboxylate |
|  | 2-Propargyl- | 2,2-Dimethyl-3-(2'- |  | 2-Propargyl-3-methyl-2-cyclo- |

-continued

| No. | Alcohol | Acid chloride/ester | Method | Cyclopropanecarboxylic acid ester obtained |
|---|---|---|---|---|
| 13 | 3-methyl-2-cyclopentene-1-one-4-ol | 2,2-Dimethyl-3-(2'-methyl-1',3'-butadienyl)-cyclopropanecarboxylic acid chloride | A | 3-methyl-2-cyclopentene-1-one-4-yl 2',2'-dimethyl-3'-(2''-methyl-1'',3''-butadienyl)-cyclopropanecarboxylate |
| 14 | N-Chloromethyl-3,4,5,6-tetrahydrophthalimide | 2,2-Dimethyl-3-(2'-methyl-1',3'-butadienyl)-cyclopropanecarboxylic acid | D | 3,4,5,6-Tetrahydrophthalimidomethyl 2',2'-dimethyl-3'-(2''-methyl-1'',3''-butadienyl)-cyclopropanecarboxylate |
| 15 | N-Hydroxymethyl-dimethyl-maleimide | 2,2-Dimethyl-3-(2'-methyl-1',3'-butadienyl)-cyclopropanecarboxylic acid chloride | A | Dimethylphthalimidomethyl 2,2-dimethyl-3-(2'-methyl-1',3'-butadienyl)-cyclopropanecarboxylate |
| 16 | 3-Chloro-4-phenyl-2-butene-1-ol | 2,2-Dimethyl-3-(2'-methyl-1',3'-butadienyl)-cyclopropanecarboxylic acid chloride | A | 3-Chloro-4-phenyl-2-butene-1-yl 2',2'-dimethyl-3'-(2''-methyl-1'',3''-butadienyl)-cyclopropanecarboxylate |
| 17 | 5-Benzyl-3-furylmethyl alcohol | 2,2-Dimethyl-3-(2'-methyl-1',3'-pentadienyl)-cyclopropanecarboxylic acid chloride | A | 5-Benzyl-3-furylmethyl 2',2'-dimethyl-3'-(2''-methyl-1'',3''-pentadienyl)-cyclopropanecarboxylate |
| 18 | 5-Propargylfurfuryl alcohol | 2,2-Dimethyl-3-(2'-methyl-1',3'-pentadienyl)-cyclopropanecarboxylic acid chloride | A | 5-Proprgylfurfuryl 2',2'-dimethyl-3'-(2''-methyl-1'',3''-pentadienyl)-cyclopropanecarboxylate |
| 19 | 3-Phenoxybenzyl alcohol | 2,2-Dimethyl-3-(2'methyl-1',3'-pentadienyl)-cyclopropanecarboxylic acid chloride | A | 3-Phenoxybenzyl 2',2'-dimethyl-3'-(2''-methyl-1'',3''-pentadienyl)-cyclopropanecarboxylate |
| 20 | 2-Allyl-3-methyl-2-cyclopentene-1-one-4-ol | 2,2-Dimethyl-3-(2'-methyl-1',3'-pentadienyl)-cyclopropanecarboxylic acid chloride | A | 2-Allyl-3-methyl-2-cyclopentene-1-one-4-yl 2',2'-dimethyl-3'-(2''-methyl-1'',3''-pentadienyl)-cyclopropanecarboxylate |
| 21 | 5-Benzyl-3-furylmethyl alcohol | Ethyl 2,2-dimethyl-3-(2',4'-dimethyl-1',3'-pentadienyl)-cyclopropanecarboxylate | E | 5-Benzyl-3-furylmethyl 2',2'-dimethyl-3'-(2'',4''-dimethyl-1'',3''-pentadienyl)-cyclopropanecarboxylate |
| 22 | 5-Propargylfurfuryl alcohol | 2,2-Dimethyl-3-(2',4'-dimethyl-1',3'-pentadienyl)-cyclopropanecarboxylic acid chloride | A | 5-propargylfurfuryl 2',2'-dimethyl-3'-(2'',4''-dimethyl-1'',3''-pentadienyl)-cyclopropanecarboxylate |
| 23 | 5-Benzyl-3-furylmethyl alcohol | 2,2-Dimethyl-3-(1',3'-butadienyl)-cyclopropanecarboxylic acid chloride | A | 5-Benzyl-3-furylmethyl 2',2'-dimethyl-3'-(1'',3''-butadienyl)-cyclopropanecarboxylate |
| 24 | 5-Benzyl-3-furylmethyl tosylate | Sodium 2,2-dimethyl-3-(1',3'-pentadienl)-cyclopropanecarboxylate | F | 5-Benzyl-3-furylmethyl 2',2'-dimethyl-3'-(1'',3''-pentadienyl)-cyclopropanecarboxylate |
| 25 | 5-Benzyl-2-furylmethyl alcohol | 2,2-Dimethyl-3-(4'-methyl-1',3'-pentadienyl)-cyclopropanecarboxylic acid chloride | A | 5-Benzyl-furylmethyl 2',2'-dimethyl-3'-(4''-methyl-1'',3''-pentadienyl)-cyclopropanecarboxylate |
| 26 | 5-Benzyl-3-furylmethyl tosylate | Sodium 2,2-dimethyl-3-(2',3'-dimethyl)-1',3'-butadienyl)-cyclopropanecarboxylate | F | 5-Benzyl-3-furylmethyl 2',2'-dimethyl-3'-(2'',3''-dimethyl-1'',3''-pentadienyl)-cyclopropanecarboxylate |
| 27 | 5-Benzyl-3-furylmethyl alcohol | 2,2-Dimethyl-3-(2',3'-dimethyl-1',3'-pentadienyl)-cyclopropanecarboxylic acid chloride | A | 5-Benzyl-3-furylmethyl 2',2'-dimethyl-3'-(2'',3''-dimethyl-1'',3''-pentadienyl)-cyclopropanecarboxylate |
| 28 | 5-Benzyl-3-furylmethyl alcohol | 2,2-Dimethyl-3-(2',3',4'-trimethyl-1',3'-pentadienyl)-cyclopropanecarboxylic acid chloride | A | 5-Benzyl-3-furylmethyl 2',2'-dimethyl-3'-(2'',3'',4''-trimethyl-1'',3''-pentadienyl)-cyclopropanecarboxylate |
| 29 | 3-(m-Tolyloxy)-2-cyanobenzyl alcohol | 2,2-Dimethyl-3-(1',3-butadienyl)-cyclopropanecarboxylic acid chloride | A | 3-(m-Tolyloxy)-2-cyanobenzyl 2',2'-dimethyl-3'-(1'',3''-butadienyl)-cyclopropanecarboxylate |

Cyclopropanecarboxylic acid ester obtained

| Yield (%) | Refractive index ($n_D^{25}$) | | C | H | N | S | Cl (%) |
|---|---|---|---|---|---|---|---|
| 85 | 1.5518 | (Found) | 78.91 | 7.37 | — | — | — |
| | | (Cal'd) | 78.83 | 7.48 | — | — | — |
| | | | (for $C_{23}H_{26}O_3$) | | | | |
| 87 | 1.5579 | (Found) | 70.86 | 6.77 | — | 9.14 | — |
| | | (Cal'd) | 70.75 | 6.79 | — | 8.99 | — |
| | | | (for $C_{21}H_{24}O_3S$) | | | | |
| 82 | 1.5763 | (Found) | 75.32 | 7.19 | — | 8.88 | — |
| | | (Cal'd) | 75.37 | 7.15 | — | 8.75 | — |
| | | | (for $C_{23}H_{26}O_2S$) | | | | |
| | | (Found) | 76.35 | 7.52 | — | — | — |

-continued

| | | | C | H | N | S | Cl |
|---|---|---|---|---|---|---|---|
| 87 | 1.5264 | (Cal'd) (for $C_{19}H_{22}O_3$) | 76.48 | 7.43 | — | — | — |
| | | (Found) | 72.81 | 7.02 | — | 10.50 | — |
| 90 | 1.5517 | (Cal'd) (for $C_{19}H_{22}O_2S$) | 72.57 | 7.05 | — | 10.20 | — |
| | | (Found) | 76.85 | 7.65 | — | — | — |
| 90 | 1.5238 | (Cal'd) (for $C_{20}H_{24}O_3$) | 76.89 | 7.74 | — | — | — |
| | | (Found) | 76.24 | 8.50 | — | — | — |
| 86 | 1.5286 | (Cal'd) (for $C_{20}H_{26}O_3$) | 76.40 | 8.34 | — | — | — |
| | | (Found) | 72.40 | 7.55 | — | 10.27 | — |
| 86 | 1.5548 | (Cal'd) (for $C_{19}H_{24}O_2S$) | 72.11 | 7.64 | — | 10.13 | — |
| | | (Found) | 79.32 | 7.18 | — | — | — |
| 92 | 1.5719 | (Calc'd) (for $C_{24}H_{26}O_3$) | 79.53 | 7.23 | — | — | — |
| | | (Found) | 79.28 | 6.47 | — | — | — |
| 89 | 1.5331 | (Cal'd) (for $C_{22}H_{22}O_3$) | 79.02 | 6.63 | — | — | — |
| | | (Found) | 77.31 | 6.62 | 3.76 | — | — |
| 85 | 1.5714 | (Cal'd) (for $C_{25}H_{25}O_3N$) | 77.49 | 6.50 | 3.62 | — | — |
| | | (Found) | 76.52 | 8.33 | — | — | — |
| 88 | 1.5278 | (Cal'd) (for $C_{20}H_{26}O_3$) | 76.40 | 8.34 | — | — | — |
| | | (Found) | 76.94 | 7.58 | — | — | — |
| 88 | 1.5340 | (Cal'd) (for $C_{20}H_{24}O_3$) | 76.89 | 7.74 | — | — | — |
| | | (Found) | 69.80 | 7.25 | 4.23 | — | — |
| 82 | 1.5415 | (Cal'd) (for $C_{20}H_{25}O_4N$) | 69.94 | 7.34 | 4.08 | — | — |
| | | (Found) | 68.40 | 7.31 | 4.35 | — | — |
| 89 | 1.5265 | (Cal'd) (for $C_{18}H_{23}O_4N$) | 68.12 | 7.30 | 4.41 | — | — |
| | | (Found) | 73.37 | 7.56 | — | — | 10.50 |
| 90 | 1.5452 | (Cal'd) (for $C_{21}H_{25}O_2Cl$) | 73.13 | 7.31 | — | — | 10.28 |
| | | (Found) | 78.95 | 7.78 | — | — | — |
| 86 | 1.5451 | (cal'd) (for $C_{24}H_{28}O_3$) | 79.09 | 7.74 | — | — | — |
| | | (Found) | 76.74 | 7.90 | — | — | — |
| 89 | 1.5194 | (Cal'd) (for $C_{20}H_{24}O_3$) | 76.89 | 7.74 | — | — | — |
| | | (Found) | 79.89 | 7.51 | — | — | — |
| 90 | 1.5655 | (Cal'd) (for $C_{25}H_{28}O_3$) | 79.75 | 7.50 | — | — | — |
| | | (Found) | 76.75 | 8.53 | — | — | — |
| 85 | 1.5213 | (Cal'd) (for $C_{21}H_{28}O_3$) | 76.79 | 8.59 | — | — | — |
| | | (Found) | 79.30 | 8.05 | — | — | — |
| 87 | 1.5249 | (Cal'd) (for $C_{25}H_{30}O_3$) | 79.33 | 7.99 | — | — | — |
| | | (Found) | 77.45 | 8.09 | — | — | — |
| 87 | 1.5182 | (Cal'd) (for $C_{21}H_{26}O_3$) | 77.29 | 8.03 | — | — | — |
| | | (Found) | 8.74 | 7.24 | — | — | — |
| 91 | 1.5436 | (Cal'd) (for $C_{22}H_{24}O_3$) | 78.54 | 7.19 | — | — | — |
| | | (Found) | 78.86 | 7.39 | — | — | — |
| 80 | 1.5418 | (Cal'd) (for $C_{23}H_{26}O_3$) | 78.83 | 7.48 | — | — | — |
| | | (Found) | 79.22 | 7.60 | — | — | — |
| 85 | 1.5445 | (Cal'd) (for $C_{24}H_{28}O_3$) | 79.09 | 7.74 | — | — | — |
| | | (Found) | 79.30 | 7.86 | — | — | — |
| 83 | 1.5480 | (Cal'd) (for $C_{24}H_{28}O_3$) | 79.09 | 7.74 | — | — | — |
| | | (Found) | 79.25 | 8.03 | — | — | — |
| 88 | 1.5425 | (Cal'd) (for $C_{25}H_{30}O_3$) | 79.33 | 7.99 | — | — | — |
| | | (Found) | 79.74 | 8.20 | — | — | — |
| 86 | 1.5473 | (Cal'd) (for $C_{26}H_{32}O_3$) | 79.55 | 8.22 | — | — | — |
| | | (Found) | 77.25 | 6.70 | 3.49 | — | — |
| 88 | 1.5640 | (Cal'd) (for $C_{25}H_{25}O_3N$) | 77.49 | 6.50 | 3.62 | — | — |

EXAMPLE 30

Into a suspension of sodium amide prepared from 6.6 g of natrium and 400 ml of liquefied ammonia, 120 g of trimethylallylphosphonium bromide was added, and the mixture was refluxed for 3 hours. A solution of 32 g of methyl trans-2,2-dimethyl-3-formyl cyclopropanecarboxylate, which was prepared according to the method by L. Crombie et al. (J.C.S. (c), 1970, 1076), in 300 ml of ether was added to the mixture, and the resultant was stirred for 2 hours and was allowed to stand to evaporate ammonia. The reaction mixture was mixed with ether, and was filtered to remove insoluble matters. After evaporation of ether, the residue was mixed with hexane, and was allowed to stand overnight in a cooler. Phosphine oxide precipitated and insoluble matters were removed by filtration. The filtrate was distilled under a reduced pressure to obtain 16.8 g of methyl trans-2,2-dimethyl-3-butadienylcyclopropanecarboxylate, b.p. 104° C/16 mmHg. It was confirmed by a gas chromatography that the configuration of the side dienyl group was cis and trans in a ratio of about 2 : 1.

EXAMPLE 31

A solution of ethyl magnesium bromide prepared from 18 g of ethyl bromide, 4 g of magnesium and 50 ml of ether was added dropwise to a solution of 32 g of methyl trans-2,2-dimethyl-3-(2'-formyl-1'-propenyl) cyclopropanecarboxylate in 200 ml of ether, while being cooled with ice. The reaction mixture was poured to an aqueous solution of sodium ammonium, whereby the objective crude alcohol was obtained in the organic layer. After evaporation of ether, the crude alcohol was dissolved in 200 ml of pyridine, and 25 g of phosphorus oxychloride was added thereto, while being cooled with ice. The reaction mixture changed immediately to black, and then the production of tar appeared. The mixture was stirred for 1 hour at 60° C. After cooling, the reaction mixture was poured onto ice water and filtered. The residue was washed with hexane, and the aqueous layer was extracted with hexane. It was confirmed by a gas chromatography that the reaction product consisted of several components. The product was purified by the rectification under a reduced pressure. The first distillate was removed and there was obtained 6.1 g to a component, which appeared to be the last peak in the gas chromatograph. The component, b.p. 104° c/0.25 mmHg, was methyl trans-2,2-dimethyl-3-(2'-methyl-1', 3'-pentadienyl)cyclopropanecarboxylate.

Procedures for preparation of the present insecticidal compositions and effects thereof are illustrated with reference to the following blending examples and examples.

BLENDING EXAMPLE 1

0.08 Part of each of the present compounds (1), (2), (3), (4), (10), (11), (14 ), (15), (16), (20), (21), (22), (32), (34), (37), (38), (41), (44), (48), (50), (51), (52), (53), (54), (55), (56), (57), (58), (59), (60), (61), (62), (68), (69), (72), (73), (74), (78), (79), (80), (90), (94), (95), (96) and (97) was dissolved in deodorized kerosene to make the total amount 100 parts, whereby oil sprays of the respective compounds were obtained.

BLENDING EXAMPLE 2

0.1 Part of each of the present compounds (5), (6), (7), (9), (23), (24), (25), (27), (28), (29), (30), (31), (39), (40), (42), (43), (45), (46), (47), (49), (63), (64), (65), (67), (81), (82), (83), (85), (86), (87), (88) and (89) was dissolved in deodorized kerosene to make the total amount 100 parts, whereby oil sprays of the respective compounds were obtained.

BLENDING EXAMPLE 3

0.2 Part of each of the present compounds (8), (12), (13), (17), (18), (19), (26), (33), (35), (36), (66), (67), (70), (71), (75), (76), (77), (84), (91), (92) and (93) was dissolved in deodorized kerosene to make the total amount 100 parts, whereby oil sprays of the respective compounds were obtained.

BLENDING EXAMPLE 4

A mixture comprising 0.05 part of the present compounds (1), (4), (6), (8), (9), (14), (15), (17), (19), (20), (21), (22), (23), (24), (25), (27), (28), (29), (30), (31), (35), (36), (37), (38), (39), (41), (42), (43), (44), (48), (49), (50), (53), (62), (64), (70), (72), (73), (76), (78), (80), (81) and (85) and 0.5 part of piperonyl butoxide was dissolved in deodorized kerosene to make the total amount 100 parts, whereby oil sprays of the respective compounds were obtained.

BLENDING EXAMPLE 5

A mixture comprising 10 parts of each of the present compounds (1), (2), (3), (4), (6), (8), (9), (10), (11), (14), (15), (16), (17), (18), (19), (20), (21), (22), (27), (28), (29), (32), (34), (35), (36), (37), (38), (41), (43), (44), (48), (50), (51), (52), (53), (54), (61), (62), (64), (66), (68), (69), (72), (73), (77), (78), (79), (80), (85), (87), (90), (92), and (93), 10 parts of Sorpol SM-200 (registered trade mark of Toho Chemical Co.) and 80 parts of xylene was thoroughly stirred to obtain emulsifiable concentrates of the respective compounds.

BLENDING EXAMPLE 6

A mixture comprising 0.4 part of the present compound (1), 2.0 parts of S-421, 6 parts of xylene and 6.6 parts of deodorized kerosene was packed in an aerosol container. After attaching a valve portion to the container, 85 parts of a propellant (liquefied petroleum gas) was introduced under pressure through said valve portion into the container to obtain an aerosol.

BLENDING EXAMPLE 7

A mixture comprising 0.4 part of the present compound (20), 0.2 part of DDVP, 7 parts of xylene and 7.4 parts of deodorized kerosene was treated in the same manner as in Blending Example 6 to obtain an aerosol.

BLENDING EXAMPLE 8

A mixture comprising 0.3 part of the present compound (85), 0.1 part of resmethrin, 2.0 parts of Sufroxane, 6 parts of xylene and 6.6 parts of deodorized kerosene was treated in the same manner as in Blending Example 6 to obtain an aerosol.

BLENDING EXAMPLE 9

A mixture comprising 0.2 part of the present compound (80), 0.2 part of Tetramethrin, 2 parts of Thanite, 6 parts of xylene and 6.6 parts of deodorized kerosene was treated in the same manner as in Blending Example 6 to obtain an aerosol.

BLENDING EXAMPLE 10

A mixture comprising 0.4 part of the present compound (6), 0.5 part of fenitrothion, 7 parts of xylene and 7.1 parts of deodorized kerosene was treated in the same manner as in Blending Example 6 to obtain an aerosol.

BLENDING EXAMPLE 11

A mixture comprising 0.3 part of the present compound (72), 0.2 part of Tetramethrin, 2 parts of piperonyl butoxide, 11.5 parts of deodorized kerosene and 1 part of an emulsifier Atmos 300 (registered trade mark of Atlas Chemical Co.) was emulsified by addition of 50 parts of pure water. Thereafter, the emulsified mixture was packed in an aerosol container together with 35 parts of a 3:1 mixture of deodorized butane and deodorized propane to obtain a water-based aerosol.

BLENDING EXAMPLE 12

A solution of 0.6 g. of each of the present compounds (6), (9), (20), (23), (25), (31), (39), (42), (45), (64), (67), (78), (81), (83) and (89) in 20 ml. of methanol was uniformly mixed with a mosquito coil carrier (a 3:5:1 mixture of Tabu powder, pyrethrum marc and wood flour). After vaporizing the methanol, the mixture was thoroughly kneaded with 150 ml. of water, and then shaped and dried to obtain mosquito coils of the respective compounds.

BLENDING EXAMPLE 13

A solution of 0.3 g. of the present compound (50) and 0.3 g. of allethrin in 20 ml. of methanol was treated in the same manner as in Blending Example 11 to obtain a mosquito coil.

BLENDING EXAMPLE 14

A solution of 0.2 g. of the present compound (78) and 0.05 g. of 5-propargylfurfuryl chrysanthemate in a suitable amount of chloroform was applied to an asbestos piece of 2.5 cm × 1.5 cm. in area and 0.3 mm. in thickness to obtain a fibrous fumigant insecticidal composition for use on a hot plate.

As the fibrous carrier, there may be used, in addition to the asbestos piece, a pulp sheet or the like material which is equivalent in effectiveness thereto.

BLENDING EXAMPLE 15

A mixture comprising 5 parts of each of the present compounds (1), (3), (14), (15), (20), (22), (50), (61), (64), (66), (72) and (80), 5 parts of Toyolignin CT (registered trade mark of Toyo Spinning Co.) and 90 parts of GSM clay (registered trade mark of Zieglite Mining Co.) was thoroughly stirred in a mortar. Subsequently, the mixture was kneaded with 10%, based on the amount of said mixture, of water and granulated by means of a granulator, followed by air-drying, to obtain granules of the respective compounds.

BLENDING EXAMPLE 16

To a solution of 1 part of the present compounds (1), (3), (10), (14), (15), (20), (22), (23), (24), (27), (50), (51), (53), (56), (73) and (80), and 3 parts of piperonyl butoxide in 20 parts of acetone was added 96 parts of 300-mesh diatomaceous earth. The resulting mixture was thoroughly stirred in a mortar, and then the acetone was vaporized to obtain dusts of the respective compounds.

BLENDING EXAMPLE 17

A mixture comprising 20 parts of each of the present compounds (4), (8), (22), (50), (72) and (85), 5 parts of 1-naphthyl-N-methylcarbamate and 5 parts of Sorpol SM-200 was thoroughly stirred in a mortar to obtain wettable powders of the respective compounds.

BLENDING EXAMPLE 18

A mixture comprising 5 parts of each of the present compounds (1), (4), (8), (15), (22), (50), (62), (73), (80), (85), (94) and (96), 25 parts of fenitrothion, 15 parts of Sorpol SM-200 and 55 parts of xylene was thoroughly stirred to obtain emulsifiable concentrates of the respective compounds.

BLENDING EXAMPLE 19

A mixture comprising 20 parts of each of the present compounds (1), (3), (14), (18), (22), (27), (35), (36), (37), (41), (48), (66), (73), (80), (85) and (93), 10 parts of Salithion, 10 parts of Sorpol SM-200 and 60 parts of xylene was thoroughly stirred to obtain emulsifiable concentrates of the respective compounds.

BLENDING EXAMPLE 20

A mixture comprising 20 parts of each of the present compounds (1), (4), (8), (15), (22), (27), (66), (72), (73), (78), (80), (81) and (85), 20 parts of Cyanox, 10 parts of Sorpol SM-200 and 50 parts of xylene was thoroughly stirred to obtain emulsifiable concentrates of the respective compounds.

Insecticidal effects of the thus obtained compositions of the present invention are as set forth in the examples shown below. These effects are observed also in the case of geometrical and optical isomers of the present compounds.

EXAMPLE 29

According to the Campbell's turn table method [disclosed in "Soap & Sanitary Chemicals", Vol. 14, No. 6, page 119 (1938)], 5 ml. of each of the oil sprays obtained in Blending Examples 1, 3 and 4 was sprayed, and adults of house flies (a group of about 100 flies) were exposed to the settling mist for 10 minutes. Thereafter, the flies were taken out, fed and allowed to stand, whereby more than 90% of the flies could be killed on the next day with every oil spray.

EXAMPLE 30

Each of the emulsifiable concentrates obtained in Blending Example 5 was diluted with water to 20,000 times, and 2 liters of the resulting emulsion was charged into a polystyrol-made case of 23 cm. × 30 cm. in size and 6 cm. in depth. subsequently, about 100 full-grown larvae of Northern house mosquitoes were liberated in the case, whereby more than 90% of the larvae could be killed on the next day with every emulsion.

EXAMPLE 31

Into a 14 liter-polyethylene bucket containing 10 liters of water was charged 1 g. of each of the granules obtained in Blending Example 15. After 1 day, about 100 full-grown larvae of Northern house mosquitoes were liberated in the water, and then the alive and dead of the larvae were observed. As the result, more than 90% of the larvae could be killed within 24 hours with every granule.

EXAMPLE 32

Insecticidal effects on house fly adults of the aerosols obtained in Blending Examples 6, 7, 8, 9, 10 and 11 were tested according to the aerosol test method disclosed in Soap & Chemical Specialities, Blue Book (1965), using a Peet Grady's chamber. The results obtained were as set forth in the following table.

| Composition | Sprayed amount (g/1,000 ft³) | Knock down ratio (%) | | | Ratio of killed insects % |
|---|---|---|---|---|---|
| | | 5 min. | 10 min. | 15 min. | |
| Aerosol of Blending Example 6 | 3.1 | 20 | 51 | 87 | 80 |
| Aerosol of Blending Example 7 | 3.0 | 34 | 65 | 90 | 84 |
| Aerosol of Blending Example 8 | 3.0 | 33 | 69 | 90 | 75 |
| Aerosol of Blending Example 9 | 2.9 | 31 | 76 | 94 | 80 |
| Aerosol of Blending Example 10 | 3.2 | 25 | 56 | 90 | 89 |
| Water-based aerosol of Blending Example 11 | 3.1 | 32 | 70 | 95 | 93 |

EXAMPLE 33

About 50 adults of Northern house mosquitoes were liberated in a (70 cm)³ glass chamber, and 0.7 ml. of each of the oil sprays obtained in Blending Example 2 was sprayed into the chamber under a pressure of 1.5 kg/cm² by use of a glass-made atomizer, whereby more than 80% of the mosquito adults could be killed within 10 minutes with every oil spray.

EXAMPLE 34

About 50 adults of Northern house mosquitoes were liberated in a (70 cm)³ glass chamber, and a battery-driven small motor fan (13 cm. in blade diameter) was placed in the chamber and rotated. Subsequently, 0.5 g. of each of the mosquito coils obtained in Blending Examples 12 and 13 was ignited on both ends and put in the chamber, whereby more than 80% of the mosquitoes could be knocked down within 20 minutes with every mosquito coil.

EXAMPLE 35

About 50 adults of house flies were liberated in a (70 cm)³ glass chamber, and a battery-driven small motor fan (13 cm. in blade diameter) was placed in the chamber and rotated. Subsequently, the heating fumigant composition obtained in Blending Example 14 was placed on an electrically heated plate and fumigated in the chamber, whereby more than 80% of the flies could be knocked down within 20 minutes.

EXAMPLE 36

Onto the bottom of a glass Petri dish of 14 cm. in diameter was uniformly dusted 2 g/m² of each of the dusts obtained in Blending Example 16, and the dish was coated on the inner wall with butter, leaving at the lower part an uncoated portion of about 1 cm. in width. Subsequently, a group of 10 German cockroach adults were liberated in the dish and contacted with the dust for 60 minutes. As the result, more than 80% of the cockroaches were knocked down with every dust, and more than 70% of the knocked-down cockroaches could be killed on the third day after the contact.

EXAMPLE 37

100 Grams of unhulled rice grains were thoroughly mixed with 100 mg. of each of the dusts obtained in Blending Example 16, and the resulting mixture was charged into a 100 ml. glass Erlenmeyer flask. Into the flask were liberated about 50 rice weevils, and then the flask was covered, whereby more than 80% of the weevils could be killed within 1 week.

EXAMPLE 38

Rice plants, which had elapsed 45 days after sowing, were grown in 1/50,000 Wagner pots. On the other hand, the emulsifiable concentrates obtained in Blending Example 5 and the wettable powders obtained in Blending Example 17 were individually diluted with water to 200 times. Each of the resulting dilutions was sprayed to the rice plants in a proportion of 10 ml/pot. Subsequently, each pot was covered with a wire net, and about 30 adults of green rice leafhoppers were liberated in the net, whereby 100% of the leafhoppers could be killed on the next day.

EXAMPLE 39

Into a glass Petri dish of 14 cm. in diameter were liberated 10 tobacco cutworm larvae of the 3-4 instar. On the other hand, the emulsifiable concentrates obtained in Blending Examples 5, 18 and 19 were individually diluted with water to 200 times. Subsequently, 1 ml. of each of the resulting dilutions was sprayed to the larvae. Thereafter, the larvae were allowed to stand in a Petri dish, in which baits had previously been placed. As the result, more than 90% of the larvae could be killed after 2 days.

EXAMPLE 40

Cabbage seedlings, which had elapsed one month after sowing, were parasitized with a large number of aphides (Myzus persica) and placed on a turn table for spraying. On the other hand, the emulsifiable concentrates obtained in Blending Examples 5, 18, 19 and 20 were individually diluted with water to 200 times. Subsequently, each of the resulting dilutions was sprayed to the seedlings in a proportion of 3 ml. per root, whereby more than 80% of the aphides could be killed after 1 day.

EXAMPLE 41

The emulsifiable concentrates obtained in Blending Example 5 were individually diluted with water to 50 times and 200 times. In each of the resulting dilutions were dipped for 1 minute tomato seedlings which had elapsed one month after sowing. After air-drying, the seedlings were transferred to a plastic-made vessel equipped with a cover, and lady beetles (*Epilachna vigintioctopunctata*) were liberated in the vessel, whereby more than 80% of the beetles could be killed after 5 days with every 50-time dilution. Most of the beetles survived when the seedlings had been dipped in the 200-time dilutions. Nevertheless, the seedlings were scarcely attacked as compared with untreated tomato seedlings, and thus displayed repelling effects.

EXAMPLE 42

Potted rice plants, which had elapsed 40 days after germination, were dusted by use of a bell jar duster with each of the dusts obtained in Blending Example 16 in a proportion of 3 kg/10 ares. Thereafter, each pot was covered with a glass cylinder, and 30 adults of green rice leafhoppers were liberated therein. Subsequently, the number of knocked down insects was counted. As the result, more than 90% of the adults were knocked down within 60 minutes with every dust.

What is claimed is:

1. A compound of the formula,

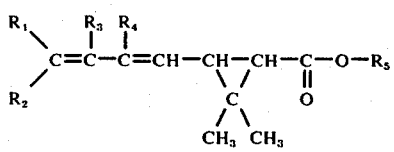

wherein $R_1$, $R_2$, $R_3$ and $R_4$ are respectively hydrogen atom or methyl, $R_5$ is

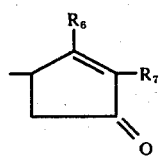

wherein $R_6$ is hydrogen atom or methyl and $R_7$ is alkenyl, alkadienyl, alkynyl or benzyl.

2. The compound according to claim 1, wherein each $R_1$, $R_2$, $R_3$ and $R_4$ is hydrogen atom.

3. The compound according to claim 1, wherein each $R_1$, $R_2$ and $R_3$ is hydrogen atom, and $R_4$ is methyl group.

4. A compound according to claim 1 which is 2-allyl-3-methyl-2-cyclopentene-1-one-4-yl 2', 2'-dimethyl-3'-(1'', 3''-butadienyl)-cyclopropanecarboxylate.

* * * * *